United States Patent [19]

Zasloff et al.

[11] Patent Number: 5,518,912
[45] Date of Patent: May 21, 1996

[54] ENDOPEPTIDASE

[75] Inventors: Michael A. Zasloff, Merion; Nicole Resnick, Lansdowne, both of Pa.

[73] Assignee: The Children's Hospital of Philadelphia, Philadelphia, Pa.

[21] Appl. No.: 132,767

[22] Filed: Oct. 6, 1993

Related U.S. Application Data

[63] Continuation of Ser. No. 2,109, Jan. 7, 1993, abandoned, which is a continuation of Ser. No. 685,723, Apr. 12, 1991, abandoned.

[51] Int. Cl.$^6$ ............................ C12N 9/64; C12N 15/57; C12N 15/10; C07K 1/00
[52] U.S. Cl. .................... 435/226; 435/68.1; 435/69.1; 435/172.3; 536/23.2; 935/14
[58] Field of Search ................................ 435/68.1, 69.1, 435/172.3, 226; 536/23.2; 935/14

[56] References Cited

PUBLICATIONS

Docherty, et al., "Proinsulin endopeptidase substrate specificities defined by site-directed mutagenesis of proinsulin," *J. Biol. Chem.* 264, 18335–18339 (1989).
Gomez et al.,"Site-specific mutagenesis identifies amino acid residues critical in prohormone processing," *EMBO J.* 8, 2911–2916 (1989).
Thorne, et al., "An in vivo characterization of the cleavage site specificity of the insulin cell prohormone processing enzymes," *J. Biol. Chem.* 265, 8436–8443 (1990).
Rholam, et al., "Precursors for peptide hormones share common secondary structures forming features at the proteolytic processing sites," *FEBS Lett.* 207, 1–6 (1986).
Bek, et al., "Prohormonal cleavage sites are associated with omega loops," *Biochem.* 29, 178–183 (1990).
von Heijne, et al., "Patterns of amino acids near signal-sequence cleavage sites," *Eur. J. Biochem.* 133, 17–21 (1983).
Duffaud, et al., "Signal peptidases recognize a structural feature at the cleavage site of secretory proteins," *J. Biol. Chem.* 263, 10224–10228 (1988).
Folz, et al., "Substrate specificity of eucaryotic signal peptidase," *J. Biol. Chem.* 263, 2070–2078 (1988).
Caulfield et al., "Synthetic substrate for eucaryotic signal peptidase," *J. Biol. Chem.* 264, 15813–15817 (1989).
Checler, et al., "Purification and characterization of novel neurotensin-degrading peptidase from rat brain synaptic membranes," *J. Biol. Chem.* 261, 11274–11281 (1986).
Clamagirand, et al., "Partial purification and functional properties of an endoprotease from bovine neurosecretory granules cleaving procytocin/neurophysin peptides at the basic amino acid doublet," *Biochem.* 26, 6018–6023 (1987).
Gluschankof, et al., "Role of peptide substrate structure in the selective processing of peptide prohormones at basic amino acid pairs by endoproteases," *FEBS Lett.* 234, 149–152 (1988).
Loh, et al., "Proteolysis in neuropeptide processing and other neural functions," *Annu. Rev. Neuro.* 7, 189–222 (1984).

Beinfeld, et al., "Characterization of an endoprotease from rat small intestinal mucosal secretory granules which generates somatostatin-28 from prosomatostatin by cleavage after a single arginine residue," *J. Biol. Chem.* 264, 4460–4465 (1989).
Brakch, et al., "Processing endoprotease recognizes a structural feature at the cleavage site of peptide prohormones," *J. Biol. Chem.* 264, 15912–15916 (1989).
Hurt, et al., "Amino-terminal deletions in the presequence of an imported mitochondrial protein block the targeting function and proteolytic cleavage of the presequence at the carboxy terminus," *J. Biol. Chem.* 262, 1420–1424 (1987).
Zasloff, et al., "Antimicrobial activity of synthetic magainin peptides and several analogues," *Proc. Natl. Acad. Sci. USA* 85, 910–913 (1988).
Bevins, et al., "Peptides from frog skin," *Annu. Rev. Biochem.* 59, 395–414 (1990).
Giovannini, et al., "Biosynthesis and degradation of peptides derived from *Xenopus laevis* prohormones," *Biochem. J.* 243, 113–120 (1987).
Richter, et al., "Sequence of preprocaerulein cDNAs cloned from skin of Xenpus laevis," *J. Biol. Chem.* 261, 3676–3680 (1986).
Poulter, et al., "Levitide, a neurohormone-like peptide from the skin of Xenopus laevis," *J. Biol. Chem.* 263, 3279–3283 (1988).
Gibson, et al., "Novel peptide fragments originating from PGLa and the caerulein and xenopsin precursors from Xenopus laevis," *J. Biol. Chem.* 261, 5341–5349 (1986).
Deutscher, M. (Ed.) "Methods in Enzymology" vol. 182 pp. 9–15, 285–421, 459–477, 602–613, 738–751 pub. 1990 by Acad. Press Inc.
Kullmann, W. "Enzymatic Peptide Synthesis" pub. 1987 by CRC Press, Inc. pages-Preface, 37,–40, 61–82.
Kimmel et al. "Methods in Enzymology" vol. 152 pub. 1987 by Acad. Press Inc. pp. 661–704.
Belyavsky, A. et al. "PCR based cDNA Library Construction . . . " Nuc. Acids. Res. vol. 17 pp. 2919–2932 (Apr. 1989).
Deutscher, M. (ed.) Meth. in Enzymology vol. 182 pp. 9–15, 285–421, 459–477, 603–613, 738–751 (1990).
Kimmel et al. Meth. in Enzymology vol. 152 pp. 661–704 (1987).
Belyansky et al. Nuc. Acids Res. 17:2919–2932 (1989).

*Primary Examiner*—Robert A. Wax
*Assistant Examiner*—Rebecca Prouty
*Attorney, Agent, or Firm*—Woodcock, Washburn, Kurtz, Mackiewicz & Norris

[57] ABSTRACT

There is provided by the invention a novel composition comprising, in at least partially purified form, an endopeptidase endogenous to biological cells. The endopeptidase is characterized by having a molecular weight of about 110,000 daltons as measured by SDS PAGE; by being substantially insensitive to PMSF, TPCK, E-64, leupeptin, bacitracin, phosphoramidon and pepstatin; by being substantially inhibited by EDTA and 1,10-phenanthroline; and by being capable of cleaving peptide substrates comprising an alpha helical structural of at least about twelve to fourteen amino acids wherein said helix has a hydrophobic face and a hydrophilic face, said cleavage occuring amino terminal to a lysine or arginine residue on the hydrophilic face positioned within the context of at least four nonpolar amino acids substantially aligned along the hydrophobic face of the helix.

6 Claims, 16 Drawing Sheets

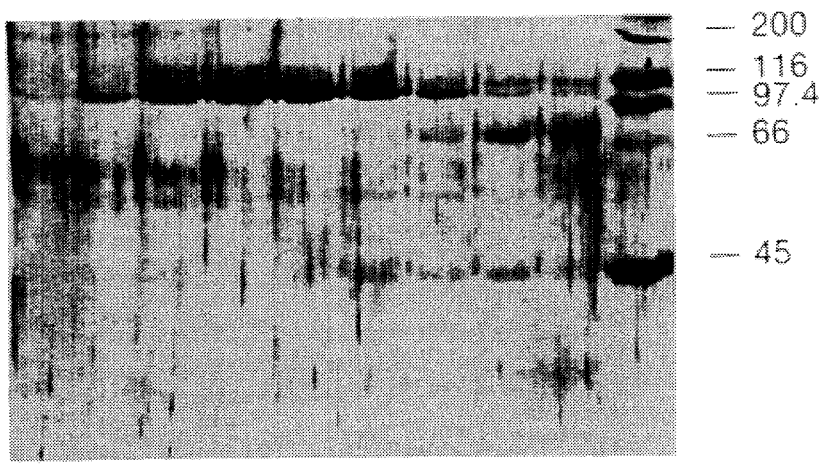
FIG. 3A
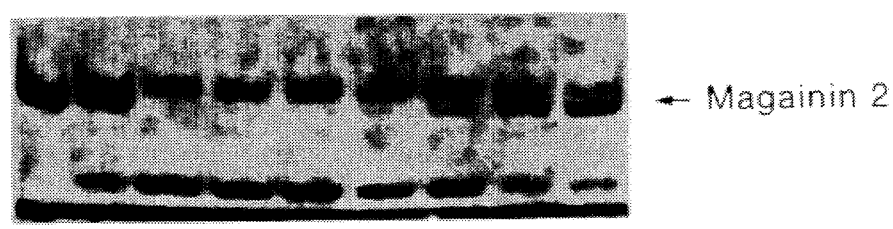
FIG. 3B ← Magainin 2
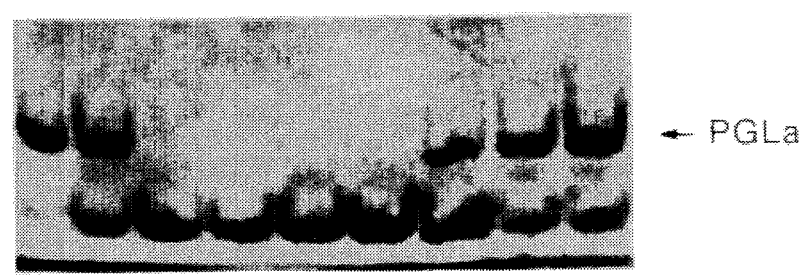
FIG. 3C ← PGLa
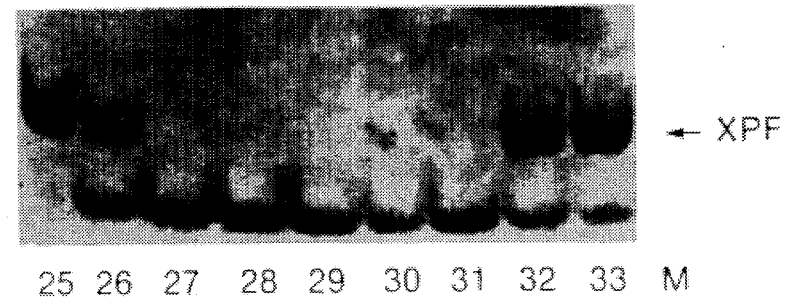
FIG. 3D ← XPF
25 26 27 28 29 30 31 32 33 M

FIG.11a  Natural substrates from Xenopus laevis magainin 2    GIGKFLHSAK ↓ KFGKAFVGEIMNS PGLa    GMASKAGAIAG ↓ KIAKVALKAL

XPF    GWASKIGQTLG ↓ KIAKVGLKELIQPK

CPF    GFASFLGKAL ↓ KAALKIGANLLGGTPQQ

FIG.11b  Magainin 2 amino-terminal truncations

| | | Relative cleavage |
|---|---|---|
| Des-1 | -IGKFLHSAK<u>K</u>FGKAFVGEIMNS | + |
| Des-1-2 | --GKFLHSAKKFGKAFVGEIMNS | − |
| Des-1-3 | ---KFLHSAKKFGKAFVGEIMNS | − |
| Des-1-4 | ----FLHSAKKFGKAFVGEIMNS | − |

Magainin 2 carbox-terminal truncations

| | | |
|---|---|---|
| Des-22-23 | GIGKFLHSA<u>KK</u>FGKAFVGEIM-- | +++ |
| Des-20-23 | GIGKFLHSA<u>KK</u>FGKAFVGE--- | +++ |
| Des-18-23 | GIGKFLHSA<u>KK</u>FGKAFV------ | +++ |

FIG.11c  Magainin 2 omission analogues
(Des-1 to Des-23)

| Sequence | Activity |
|---|---|
| IGKFLHSA<u>KK</u>FGKAFVGEIMNS | + |
| G GKFLHSA<u>KK</u>FGKAFVGEIMNS | + |
| GI KFLHSA<u>KK</u>FGKAFVGEIMNS | + |
| GIG FLHSA<u>KK</u>FGKAFVGEIMNS | + |
| GIGK LHSA<u>KK</u>FGKAFVGEIMNS | + |
| GIGKF HSA<u>KK</u>FGKAFVGEIMNS | + |
| GIGKFL SA<u>KK</u>FGKAFVGEIMNS | + |
| GIGKFLH A<u>KK</u>FGKAFVGEIMNS | + |
| GIGKFLHS <u>KK</u>FGKAFVGEIMNS | + |
| GIGKFLHSA <u>K</u>FGKAFVGEIMNS | + |
| GIGKFLHSA<u>K</u> FGKAFVGEIMNS | + |
| GIGKFLHSA<u>KK</u> GKAFVGEIMNS | + |
| GIGKFLHSA<u>KK</u>F KAFVGEIMNS | + + |
| GIGKFLHSA<u>KK</u>FG AFVGEIMNS | + + + |
| GIGKFLHSA<u>KK</u>FGK FVGEIMNS | + + + |
| GIGKFLHSA<u>KK</u>FGKA VGEIMNS | + + + |
| GIGKFLHSA<u>KK</u>FGKAF GEIMNS | + + + |
| GIGKFLHSA<u>KK</u>FGKAFV EIMNS | + + + |
| GIGKFLHSA<u>KK</u>FGKAFVG IMNS | + + + |
| GIGKFLHSA<u>KK</u>FGKAFVGE MNS | + + + |
| GIGKFLHSA<u>KK</u>FGKAFVGEI NS | + + + |
| GIGKFLHSA<u>KK</u>FGKAFVGEIM S | + + + |
| GIGKFLHSA<u>KK</u>FGKAFVGEIMN | + + + |

FIG.11d  Magainin 1 glutamate substitutions

| Sequence | Activity |
|---|---|
| EIGKFLHSAGKFGKAFVGEIMKS | − |
| GEGKFLHSA<u>GK</u>FGKAFVGEIMKS | + + |
| GIEKFLHSA<u>GK</u>FGKAFVGEIMKS | + + |
| GIGEFLHSA<u>GK</u>FGKAFVGEIMKS | + + + |
| GIGKELHSA<u>GK</u>FGKAFVGEIMKS | + |
| GIGKFEHSA<u>GK</u>FGKAFVGEIMKS | ++++ |
| GIGKFLESA<u>GK</u>FGKAFVGEIMKS | ++++ |
| GIGKFLHEA<u>GK</u>FGKAFVGEIMKS | + + + |
| GIGKFLHSE<u>GK</u>FGKAFVGEIMKS | + |
| GIGKFLHSAE<u>K</u>FGKAFVGEIMKS | ++++ |
| GIGKFLHSAGE FGKAFVGEIMKS | − |
| GIGKFLHSAGKEGKAFVGEIMKS | − |

FIG.11e  PGLa omission analogues

| | | |
|---|---|---|
| Des-Lys⁵ | GMAS AGAIAGKIAKVALKAL | ++++ |
| Des--Gly¹¹ | GMASKAGAIA KIAKVALKAL | ++ |
| Des-Lys¹² | GMASKAGAIAG IAKVALKAL | – |

FIG.11f  Magainin cleavage site substitutions

| | | |
|---|---|---|
| K11R | GIGRFLRSAGRFGRAFVRILNS | ++ |
| K11E | GIGKFLHSAGEFGKAFVGEIMKS | – |
| K11A | GIGKFLHSAGAFGKAFVGEIMKS | – |
| K11P | GIGKFLHSAGPFGKAFVGEIMKS | – |
| G10A | GIGKFLHSAAKFGKAFVGEIMKS | +++ |
| G10E | GIGKFLHSAEKFGKAFVGEIMKS | +++ |
| G10P | GIGKFLHSAPKFGKAFVGEIMKS | – |

FIG.11g  Magainin 2 cleavage site chirality analogues

| | | |
|---|---|---|
| dK11 | GIGKFLHSAKdKFGKAFVGEIMNS | +++ |
| dK10 | GIGKFLHSAdKKFGKAFVGEIMNS | ++ |

FIG.11h  Magainin 2 amino-terminal extension

| | | |
|---|---|---|
| REVR(1-4) | REVRGIGKFLHSAKKFGKAFVGEIMNS | +++ |

FIG.11i  Miscellaneous amphipathic alpha-helical peptides

| | | |
|---|---|---|
| melitin | GIGAVLKVLTTGLPALISWIKKKKQQ | – |

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
    ( A ) LENGTH: 23
    ( B ) TYPE: Amino acids
    ( D ) TOPOLOGY: Unknown ( x i ) SEQUENCE DESCRIPTION: SEQ ID NO:1:

Gly Ile Gly Lys Phe Leu His Ser Ala Lys Lys Phe Gly Lys Ala
1               5                   10                  15
Phe Val Gly Glu Ile Met Asn Ser
                20

( 2 ) INFORMATION FOR SEQ ID NO:2:

( i ) SEQUENCE CHARACTERISTICS:
        ( A ) LENGTH: 21
        ( B ) TYPE: Amino acids
        ( D ) TOPOLOGY: Unknown ( x i ) SEQUENCE DESCRIPTION: SEQ ID NO:2:

Gly Met Ala Ser Lys Ala Gly Ala Ile Ala Gly Lys Ile Ala Lys
1               5                   10                  15
Val Ala Leu Lys Ala Leu
                20

( 2 ) INFORMATION FOR SEQ ID NO:3:

( i ) SEQUENCE CHARACTERISTICS:
        ( A ) LENGTH: 25
        ( B ) TYPE: Amino acids
        ( D ) TOPOLOGY: Unknown ( x i ) SEQUENCE DESCRIPTION: SEQ ID NO:3:

Gly Trp Ala Ser Lys Ile Gly Gln Thr Leu Gly Lys Ile Ala Lys
1               5                   10                  15
Val Gly Leu Lys Glu Leu Ile Gln Pro Lys
                20                  25

( 2 ) INFORMATION FOR SEQ ID NO:4:

( i ) SEQUENCE CHARACTERISTICS:
        ( A ) LENGTH: 27
        ( B ) TYPE: Amino acids
        ( D ) TOPOLOGY: Unknown ( x i ) SEQUENCE DESCRIPTION: SEQ ID NO:4:

Gly Phe Ala Ser Phe Leu Gly Lys Ala Leu Lys Ala Ala Leu Lys
1               5                   10                  15
Ile Gly Ala Asn Leu Leu Gly Gly Thr Pro Gln Gln
                20                  25

( 2 ) INFORMATION FOR SEQ ID NO:5:

( i ) SEQUENCE CHARACTERISTICS:
        ( A ) LENGTH: 22
        ( B ) TYPE: Amino acids
        ( D ) TOPOLOGY: Unknown ( x i ) SEQUENCE DESCRIPTION: SEQ ID NO:5:

Ile Gly Lys Phe Leu His Ser Ala Lys Lys Phe Gly Lys Ala Phe
1               5                   10                  15
Val Gly Glu Ile Met Asn Ser
                20

( 2 ) INFORMATION FOR SEQ ID NO:6:

(i) SEQUENCE CHARACTERISTICS:
    (A) LENGTH: 21
    (B) TYPE: Amino acids
    (D) TOPOLOGY: Unknown (xi) SEQUENCE DESCRIPTION: SEQ ID NO:6:

Gly Lys Phe Leu His Ser Ala Lys Lys Phe Gly Lys Ala Phe Val
1               5                   10                  15
Gly Glu Ile Met Asn Ser
                20

(2) INFORMATION FOR SEQ ID NO:7:

(i) SEQUENCE CHARACTERISTICS:
        (A) LENGTH: 20
        (B) TYPE: Amino acids
        (D) TOPOLOGY: Unknown (xi) SEQUENCE DESCRIPTION: SEQ ID NO:7:

Lys Phe Leu His Ser Ala Lys Lys Phe Gly Lys Ala Phe Val Gly
1               5                   10                  15
Glu Ile Met Asn Ser
                20

(2) INFORMATION FOR SEQ ID NO:8:

(i) SEQUENCE CHARACTERISTICS:
        (A) LENGTH: 19
        (B) TYPE: Amino acids
        (D) TOPOLOGY: Unknown (xi) SEQUENCE DESCRIPTION: SEQ ID NO:8:

Phe Leu His Ser Ala Lys Lys Phe Gly Lys Ala Phe Val Gly Glu
1               5                   10                  15
Ile Met Asn Ser (2) INFORMATION FOR SEQ ID NO:9:

(i) SEQUENCE CHARACTERISTICS:
        (A) LENGTH: 21
        (B) TYPE: Amino acids
        (D) TOPOLOGY: Unknown (xi) SEQUENCE DESCRIPTION: SEQ ID NO:9:

Gly Ile Gly Lys Phe Leu His Ser Ala Lys Lys Phe Gly Lys Ala
1               5                   10                  15
Phe Val Gly Glu Ile Met
                20

(2) INFORMATION FOR SEQ ID NO:10:

(i) SEQUENCE CHARACTERISTICS:
        (A) LENGTH: 19
        (B) TYPE: Amino acids
        (D) TOPOLOGY: Unknown (xi) SEQUENCE DESCRIPTION: SEQ ID NO:10:

Gly Ile Gly Lys Phe Leu His Ser Ala Lys Lys Phe Gly Lys Ala
1               5                   10                  15
Phe Val Gly Glu (2) INFORMATION FOR SEQ ID NO:11:

(i) SEQUENCE CHARACTERISTICS:

(A) LENGTH: 17
(B) TYPE: Amino acids
(D) TOPOLOGY: Unknown (xi) SEQUENCE DESCRIPTION: SEQ ID NO:11:

Gly Ile Gly Lys Phe Leu His Ser Ala Lys Lys Phe Gly Lys Ala
1               5                   10                  15
Phe Val (2) INFORMATION FOR SEQ ID NO:12:

(i) SEQUENCE CHARACTERISTICS:
(A) LENGTH: 22
(B) TYPE: Amino acids
(D) TOPOLOGY: Unknown (xi) SEQUENCE DESCRIPTION: SEQ ID NO:12:

Ile Gly Lys Phe Leu His Ser Ala Lys Lys Phe Gly Lys Ala Phe
1               5                   10                  15
Val Gly Glu Ile Met Asn Ser
                20

(2) INFORMATION FOR SEQ ID NO:13:

(i) SEQUENCE CHARACTERISTICS:
(A) LENGTH: 22
(B) TYPE: Amino acids
(D) TOPOLOGY: Unknown (xi) SEQUENCE DESCRIPTION: SEQ ID NO:13:

Gly Gly Lys Phe Leu His Ser Ala Lys Lys Phe Gly Lys Ala Phe
1               5                   10                  15
Val Gly Glu Ile Met Asn Ser
                20

(2) INFORMATION FOR SEQ ID NO:14:

(i) SEQUENCE CHARACTERISTICS:
(A) LENGTH: 22
(B) TYPE: Amino acids
(D) TOPOLOGY: Unknown (xi) SEQUENCE DESCRIPTION: SEQ ID NO:14:

Gly Ile Lys Phe Leu His Ser Ala Lys Lys Phe Gly Lys Ala Phe
1               5                   10                  15
Val Gly Glu Ile Met Asn Ser
                20

(2) INFORMATION FOR SEQ ID NO:15:

(i) SEQUENCE CHARACTERISTICS:
(A) LENGTH: 22
(B) TYPE: Amino acids
(D) TOPOLOGY: Unknown (xi) SEQUENCE DESCRIPTION: SEQ ID NO:15:

Gly Ile Gly Phe Leu His Ser Ala Lys Lys Phe Gly Lys Ala Phe
1               5                   10                  15
Val Gly Glu Ile Met Asn Ser
                20

(2) INFORMATION FOR SEQ ID NO:16:

(i) SEQUENCE CHARACTERISTICS:
(A) LENGTH: 23

(B) TYPE: Amino acids
(D) TOPOLOGY: Unknown (xi) SEQUENCE DESCRIPTION: SEQ ID NO:16:

Gly Ile Gly Lys Leu Leu His Ser Ala Lys Lys Phe Gly Lys Ala
1               5                   10                  15
Phe Val Gly Glu Ile Met Asn Ser
                20

(2) INFORMATION FOR SEQ ID NO:17:

(i) SEQUENCE CHARACTERISTICS:
(A) LENGTH: 23
(B) TYPE: Amino acids
(D) TOPOLOGY: Unknown (xi) SEQUENCE DESCRIPTION: SEQ ID NO:17:

Gly Ile Gly Lys Phe His His Ser Ala Lys Lys Phe Gly Lys Ala
1               5                   10                  15
Phe Val Gly Glu Ile Met Asn Ser
                20

(2) INFORMATION FOR SEQ ID NO:18:

(i) SEQUENCE CHARACTERISTICS:
(A) LENGTH: 22
(B) TYPE: Amino acids
(D) TOPOLOGY: Unknown (xi) SEQUENCE DESCRIPTION: SEQ ID NO:18:

Gly Ile Gly Lys Phe Leu Ser Ala Lys Lys Phe Gly Lys Ala Phe
1               5                   10                  15
Val Gly Glu Ile Met Asn Ser
                20

(2) INFORMATION FOR SEQ ID NO:19:

(i) SEQUENCE CHARACTERISTICS:
(A) LENGTH: 22
(B) TYPE: Amino acids
(D) TOPOLOGY: Unknown (xi) SEQUENCE DESCRIPTION: SEQ ID NO:19:

Gly Ile Gly Lys Phe Leu His Ala Lys Lys Phe Gly Lys Ala Phe
1               5                   10                  15
Val Gly Glu Ile Met Asn Ser
                20

(2) INFORMATION FOR SEQ ID NO:20:

(i) SEQUENCE CHARACTERISTICS:
(A) LENGTH: 22
(B) TYPE: Amino acids
(D) TOPOLOGY: Unknown (xi) SEQUENCE DESCRIPTION: SEQ ID NO:20:

Gly Ile Gly Lys Phe Leu His Ser Lys Lys Phe Gly Lys Ala Phe
1               5                   10                  15
Val Gly Glu Ile Met Asn Ser
                20

(2) INFORMATION FOR SEQ ID NO:21:

(i) SEQUENCE CHARACTERISTICS:
(A) LENGTH: 22

( B ) TYPE: Amino acids
( D ) TOPOLOGY: Unknown ( x i ) SEQUENCE DESCRIPTION: SEQ ID NO:21:

Gly Ile Gly Lys Phe Leu His Ser Ala Lys Phe Gly Lys Ala Phe
1               5                   10                  15

Val Gly Glu Ile Met Asn Ser
                20

( 2 ) INFORMATION FOR SEQ ID NO:22:

( i ) SEQUENCE CHARACTERISTICS:
( A ) LENGTH: 22
( B ) TYPE: Amino acids
( D ) TOPOLOGY: Unknown ( x i ) SEQUENCE DESCRIPTION: SEQ ID NO:22:

Gly Ile Gly Lys Phe Leu His Ser Ala Lys Phe Gly Lys Ala Phe
1               5                   10                  15

Val Gly Glu Ile Met Asn Ser
                20

( 2 ) INFORMATION FOR SEQ ID NO:23:

( i ) SEQUENCE CHARACTERISTICS:
( A ) LENGTH: 22
( B ) TYPE: Amino acids
( D ) TOPOLOGY: Unknown ( x i ) SEQUENCE DESCRIPTION: SEQ ID NO:23:

Gly Ile Gly Lys Phe Leu His Ser Ala Lys Lys Gly Lys Ala Phe
1               5                   10                  15

Val Gly Glu Ile Met Asn Ser
                20

( 2 ) INFORMATION FOR SEQ ID NO:24:

( i ) SEQUENCE CHARACTERISTICS:
( A ) LENGTH: 22
( B ) TYPE: Amino acids
( D ) TOPOLOGY: Unknown ( x i ) SEQUENCE DESCRIPTION: SEQ ID NO:24:

Gly Ile Gly Lys Phe Leu His Ser Ala Lys Lys Phe Lys Ala Phe
1               5                   10                  15

Val Gly Glu Ile Met Asn Ser
                20

( 2 ) INFORMATION FOR SEQ ID NO:25:

( i ) SEQUENCE CHARACTERISTICS:
( A ) LENGTH: 22
( B ) TYPE: Amino acids
( D ) TOPOLOGY: Unknown ( x i ) SEQUENCE DESCRIPTION: SEQ ID NO:25:

Gly Ile Gly Lys Phe Leu His Ser Ala Lys Lys Phe Gly Ala Phe
1               5                   10                  15

Val Gly Glu Ile Met Asn Ser
                20

( 2 ) INFORMATION FOR SEQ ID NO:26:

( i ) SEQUENCE CHARACTERISTICS:
( A ) LENGTH: 22

(B) TYPE: Amino acids
(D) TOPOLOGY: Unknown (xi) SEQUENCE DESCRIPTION: SEQ ID NO:26:

Gly Ile Gly Lys Phe Leu His Ser Ala Lys Lys Phe Gly Lys Phe
1               5                   10                  15
Val Gly Glu Ile Met Asn Ser
                20

(2) INFORMATION FOR SEQ ID NO:27:

(i) SEQUENCE CHARACTERISTICS:
    (A) LENGTH: 22
    (B) TYPE: Amino acids
    (D) TOPOLOGY: Unknown (xi) SEQUENCE DESCRIPTION: SEQ ID NO:27:

Gly Ile Gly Lys Phe Leu His Ser Ala Lys Lys Phe Gly Lys Ala
1               5                   10                  15
Val Gly Glu Ile Met Asn Ser
                20

(2) INFORMATION FOR SEQ ID NO:28:

(i) SEQUENCE CHARACTERISTICS:
    (A) LENGTH: 22
    (B) TYPE: Amino acids
    (D) TOPOLOGY: Unknown (xi) SEQUENCE DESCRIPTION: SEQ ID NO:28:

Gly Ile Gly Lys Phe Leu His Ser Ala Lys Lys Phe Gly Lys Ala
1               5                   10                  15
Phe Gly Glu Ile Met Asn Ser
                20

(2) INFORMATION FOR SEQ ID NO:29:

(i) SEQUENCE CHARACTERISTICS:
    (A) LENGTH: 22
    (B) TYPE: Amino acids
    (D) TOPOLOGY: Unknown (xi) SEQUENCE DESCRIPTION: SEQ ID NO:29:

Gly Ile Gly Lys Phe Leu His Ser Ala Lys Lys Phe Gly Lys Ala
1               5                   10                  15
Phe Val Glu Ile Met Asn Ser
                20

(2) INFORMATION FOR SEQ ID NO:30:

(i) SEQUENCE CHARACTERISTICS:
    (A) LENGTH: 22
    (B) TYPE: Amino acids
    (D) TOPOLOGY: Unknown (xi) SEQUENCE DESCRIPTION: SEQ ID NO:30:

Gly Ile Gly Lys Phe Leu His Ser Ala Lys Lys Phe Gly Lys Ala
1               5                   10                  15
Phe Val Gly Ile Met Asn Ser
                20

(2) INFORMATION FOR SEQ ID NO:31:

(i) SEQUENCE CHARACTERISTICS:
    (A) LENGTH: 22

(B) TYPE: Amino acids
(D) TOPOLOGY: Unknown (xi) SEQUENCE DESCRIPTION: SEQ ID NO:31:

Gly Ile Gly Lys Phe Leu His Ser Ala Lys Lys Phe Gly Lys Ala
1               5                   10                  15
Phe Val Gly Glu Met Asn Ser
                20

(2) INFORMATION FOR SEQ ID NO:32:

(i) SEQUENCE CHARACTERISTICS:
        (A) LENGTH: 22
        (B) TYPE: Amino acids
        (D) TOPOLOGY: Unknown (xi) SEQUENCE DESCRIPTION: SEQ ID NO:32:

Gly Ile Gly Lys Phe Leu His Ser Ala Lys Lys Phe Gly Lys Ala
1               5                   10                  15
Phe Val Gly Glu Ile Asn Ser
                20

(2) INFORMATION FOR SEQ ID NO:33:

(i) SEQUENCE CHARACTERISTICS:
        (A) LENGTH: 22
        (B) TYPE: Amino acids
        (D) TOPOLOGY: Unknown (xi) SEQUENCE DESCRIPTION: SEQ ID NO:33:

Gly Ile Gly Lys Phe Leu His Ser Ala Lys Lys Phe Gly Lys Ala
1               5                   10                  15
Phe Val Gly Glu Ile Met Ser
                20

(2) INFORMATION FOR SEQ ID NO:34:

(i) SEQUENCE CHARACTERISTICS:
        (A) LENGTH: 22
        (B) TYPE: Amino acids
        (D) TOPOLOGY: Unknown (xi) SEQUENCE DESCRIPTION: SEQ ID NO:34:

Gly Ile Gly Lys Phe Leu His Ser Ala Lys Lys Phe Gly Lys Ala
1               5                   10                  15
Phe Val Gly Glu Ile Met Asn
                20

(2) INFORMATION FOR SEQ ID NO:35:

(i) SEQUENCE CHARACTERISTICS:
        (A) LENGTH: 23
        (B) TYPE: Amino acids
        (D) TOPOLOGY: Unknown (xi) SEQUENCE DESCRIPTION: SEQ ID NO:35:

Glu Ile Gly Lys Phe Leu His Ser Ala Gly Lys Phe Gly lys Ala
1               5                   10                  15
Phe Val Gly Glu Ile Met Lys Ser
                20

(2) INFORMATION FOR SEQ ID NO:36:

(i) SEQUENCE CHARACTERISTICS:
        (A) LENGTH: 23

(B) TYPE: Amino acids
(D) TOPOLOGY: Unknown (xi) SEQUENCE DESCRIPTION: SEQ ID NO:36:

| Gly | Glu | Gly | Lys | Phe | Leu | His | Ser | Ala | Gly | Lys | Phe | Gly | Lys | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Phe | Val | Gly | Glu | Ile | Met | Lys | Ser |
|-----|-----|-----|-----|-----|-----|-----|-----|
|     |     |     |     | 20  |     |     |     |

(2) INFORMATION FOR SEQ ID NO:37:

(i) SEQUENCE CHARACTERISTICS:
(A) LENGTH: 23
(B) TYPE: Amino acids
(D) TOPOLOGY: Unknown (xi) SEQUENCE DESCRIPTION: SEQ ID NO:37:

| Gly | Ile | Glu | Lys | Phe | Leu | His | Ser | Ala | Gly | Lys | Phe | Gly | Lys | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Phe | Val | Gly | Glu | Ile | Met | Lys | Ser |
|-----|-----|-----|-----|-----|-----|-----|-----|
|     |     |     |     | 20  |     |     |     |

(2) INFORMATION FOR SEQ ID NO:38:

(i) SEQUENCE CHARACTERISTICS:
(A) LENGTH: 23
(B) TYPE: Amino acids
(D) TOPOLOGY: Unknown (xi) SEQUENCE DESCRIPTION: SEQ ID NO:38:

| Gly | Ile | Gly | Glu | Phe | Leu | His | Ser | Ala | Gly | Lys | Phe | Gly | Lys | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Phe | Val | Gly | Glu | Ile | Met | Lys | Ser |
|-----|-----|-----|-----|-----|-----|-----|-----|
|     |     |     |     | 20  |     |     |     |

(2) INFORMATION FOR SEQ ID NO:39:

(i) SEQUENCE CHARACTERISTICS:
(A) LENGTH: 23
(B) TYPE: Amino acids
(D) TOPOLOGY: Unknown (xi) SEQUENCE DESCRIPTION: SEQ ID NO:39:

| Gly | Ile | Gly | Lys | Glu | Leu | His | Ser | Ala | Gly | Lys | Phe | Gly | Lys | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Phe | Val | Gly | Glu | Ile | Met | Lys | Ser |
|-----|-----|-----|-----|-----|-----|-----|-----|
|     |     |     |     | 20  |     |     |     |

(2) INFORMATION FOR SEQ ID NO:40:

(i) SEQUENCE CHARACTERISTICS:
(A) LENGTH: 23
(B) TYPE: Amino acids
(D) TOPOLOGY: Unknown (xi) SEQUENCE DESCRIPTION: SEQ ID NO:40:

| Gly | Ile | Gly | Lys | Phe | Glu | His | Ser | Ala | Gly | Lys | Phe | Gly | Lys | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Phe | Val | Gly | Glu | Ile | Met | Lys | Ser |
|-----|-----|-----|-----|-----|-----|-----|-----|
|     |     |     |     | 20  |     |     |     |

(2) INFORMATION FOR SEQ ID NO:41:

(i) SEQUENCE CHARACTERISTICS:
(A) LENGTH: 23

(B) TYPE: Amino acids
        (D) TOPOLOGY: Unknown (xi) SEQUENCE DESCRIPTION: SEQ ID NO:41:

Gly Ile Gly Lys Phe Leu Glu Ser Ala Gly Lys Phe Gly Lys Ala
1               5                   10                  15
Phe Val Gly Glu Ile Met Lys Ser
                20

(2) INFORMATION FOR SEQ ID NO:42:

(i) SEQUENCE CHARACTERISTICS:
        (A) LENGTH: 23
        (B) TYPE: Amino acids
        (D) TOPOLOGY: Unknown (xi) SEQUENCE DESCRIPTION: SEQ ID NO:42:

Gly Ile Gly Lys Phe Leu His Glu Ala Gly Lys Phe Gly Lys Ala
1               5                   10                  15
Phe Val Gly Glu Ile Met Lys Ser
                20

(2) INFORMATION FOR SEQ ID NO:43:

(i) SEQUENCE CHARACTERISTICS:
        (A) LENGTH: 23
        (B) TYPE: Amino acids
        (D) TOPOLOGY: Unknown (xi) SEQUENCE DESCRIPTION: SEQ ID NO:43:

Gly Ile Gly Lys Phe Leu His Ser Glu Gly Lys Phe Gly Lys Ala
1               5                   10                  15
Phe Val Gly Glu Ile Met Lys Ser
                20

(2) INFORMATION FOR SEQ ID NO:44:

(i) SEQUENCE CHARACTERISTICS:
        (A) LENGTH: 22
        (B) TYPE: Amino acids
        (D) TOPOLOGY: Unknown (xi) SEQUENCE DESCRIPTION: SEQ ID NO:44:

Gly Ile Gly Lys Leu His Ser Ala Glu Lys Phe Gly Lys Ala Phe
1               5                   10                  15
Val Gly Glu Ile Met Lys Ser
                20

(2) INFORMATION FOR SEQ ID NO:45:

(i) SEQUENCE CHARACTERISTICS:
        (A) LENGTH: 23
        (B) TYPE: Amino acids
        (D) TOPOLOGY: Unknown (xi) SEQUENCE DESCRIPTION: SEQ ID NO:45:

Gly Ile Gly Lys Phe Leu His Ser Ala Gly Glu Phe Gly Lys Ala
1               5                   10                  15
Phe Val Gly Glu Ile Met Lys Ser
                20

(2) INFORMATION FOR SEQ ID NO:46:

(i) SEQUENCE CHARACTERISTICS:
        (A) LENGTH: 23

(B) TYPE: Amino acids
(D) TOPOLOGY: Unknown (xi) SEQUENCE DESCRIPTION: SEQ ID NO:46:

Gly Ile Gly Lys Phe Leu His Ser Ala Gly Lys Glu Gly Lys Ala
1               5                   10                  15
Phe Val Gly Glu Ile Met Lys Ser
                20

(2) INFORMATION FOR SEQ ID NO:47:

(i) SEQUENCE CHARACTERISTICS:
    (A) LENGTH: 20
    (B) TYPE: Amino acids
    (D) TOPOLOGY: Unknown (xi) SEQUENCE DESCRIPTION: SEQ ID NO:47:

Gly Met Ala Ser Ala Gly Ala Ile Ala Gly Lys Ile Ala Lys Val
1               5                   10                  15
Ala Leu Lys Ala Leu
                20

(2) INFORMATION FOR SEQ ID NO:48:

(i) SEQUENCE CHARACTERISTICS:
    (A) LENGTH: 20
    (B) TYPE: Amino acids
    (D) TOPOLOGY: Unknown (xi) SEQUENCE DESCRIPTION: SEQ ID NO:48:

Gly Met Ala Ser Lys Ala Gly Ala Ile Ala Lys Ile Ala Lys Val
1               5                   10                  15
Ala Leu Lys Ala Leu
                20

(2) INFORMATION FOR SEQ ID NO:49:

(i) SEQUENCE CHARACTERISTICS:
    (A) LENGTH: 20
    (B) TYPE: Amino acids
    (D) TOPOLOGY: Unknown (xi) SEQUENCE DESCRIPTION: SEQ ID NO:49:

Gly Met Ala Ser Lys Ala Gly Ala Ile Ala Gly Ile Ala Lys Val
1               5                   10                  15
Ala Leu Lys Ala Leu
                20

(2) INFORMATION FOR SEQ ID NO:50:

(i) SEQUENCE CHARACTERISTICS:
    (A) LENGTH: 22
    (B) TYPE: Amino acids
    (D) TOPOLOGY: Unknown (xi) SEQUENCE DESCRIPTION: SEQ ID NO:50:

Gly Ile Gly Arg Phe Leu Arg Ser Ala Gly Arg Phe Gly Arg Ala
1               5                   10                  15
Phe Val Arg Ile Leu Asn Ser
                20

(2) INFORMATION FOR SEQ ID NO:51:

(i) SEQUENCE CHARACTERISTICS:
    (A) LENGTH: 23

(B) TYPE: Amino acids
(D) TOPOLOGY: Unknown (xi) SEQUENCE DESCRIPTION: SEQ ID NO:51:

Gly Ile Gly Lys Phe Leu His Ser Ala Gly Glu Phe Gly Lys Ala
1               5                   10                  15
Phe Val Gly Glu Ile Met Lys Ser
                20

(2) INFORMATION FOR SEQ ID NO:52:

(i) SEQUENCE CHARACTERISTICS:
        (A) LENGTH: 23
        (B) TYPE: Amino acids
        (D) TOPOLOGY: Unknown (xi) SEQUENCE DESCRIPTION: SEQ ID NO:52:

Gly Ile Gly Lys Phe Leu His Ser Ala Gly Ala Phe Gly Lys Ala
1               5                   10                  15
Phe Val Gly Glu Ile Met Lys Ser
                20

(2) INFORMATION FOR SEQ ID NO:53:

(i) SEQUENCE CHARACTERISTICS:
        (A) LENGTH: 23
        (B) TYPE: Amino acids
        (D) TOPOLOGY: Unknown (xi) SEQUENCE DESCRIPTION: SEQ ID NO:53:

Gly Ile Gly Lys Phe Leu His Ser Ala Gly Pro Phe Gly Lys Ala
1               5                   10                  15
Phe Val Gly Glu Ile Met Lys Ser
                20

(2) INFORMATION FOR SEQ ID NO:54:

(i) SEQUENCE CHARACTERISTICS:
        (A) LENGTH: 23
        (B) TYPE: Amino acids
        (D) TOPOLOGY: Unknown (xi) SEQUENCE DESCRIPTION: SEQ ID NO:54:

Gly Ile Gly Lys Phe Leu His Ser Ala Ala Lys Phe Gly Lys Ala
1               5                   10                  15
Phe Val Gly Glu Ile Met Lys Ser
                20

(2) INFORMATION FOR SEQ ID NO:55:

(i) SEQUENCE CHARACTERISTICS:
        (A) LENGTH: 23
        (B) TYPE: Amino acids
        (D) TOPOLOGY: Unknown (xi) SEQUENCE DESCRIPTION: SEQ ID NO:55:

Gly Ile Gly Lys Phe Leu His Ser Ala Glu Lys Phe Gly Lys Ala
1               5                   10                  15
Phe Val Gly Glu Ile Met Lys Ser
                20

(2) INFORMATION FOR SEQ ID NO:56:

(i) SEQUENCE CHARACTERISTICS:
        (A) LENGTH: 23

( B ) TYPE: Amino acids
( D ) TOPOLOGY: Unknown ( x i ) SEQUENCE DESCRIPTION: SEQ ID NO:56:

```
Gly  Ile  Gly  Lys  Phe  Leu  His  Ser  Ala  Pro  Lys  Phe  Gly  Lys  Ala
1               5                        10                       15
Phe  Val  Gly  Glu  Ile  Met  Lys  Ser
                    20
```

ENDOPEPTIDASE

This is a continuation of application Ser. No. 08/002,109, filed Jan. 7, 1993, now abandoned which, in turn, is a Continuation of Ser. No. 07/685,723, filed Apr. 12, 1991, now abandoned.

FIELD OF THE INVENTION

This invention relates to a proteolytic enzyme. More particularly, this invention relates to a proteolytic endopeptidase derivable from the skin of *Xenopus laevis*.

BACKGROUND OF THE INVENTION

The initial synthesis of hormones and neuropeptides as large polypeptide precursors following synthesis is a widespread phenomenon that has been demonstrated in organisms from yeast to mammals. The post-translational liberation of bioactive molecules from their propeptide structures requires a host of processing enzymes that also appear to be conserved across eucaryotes.

The first step in the production of mature peptides and hormones, endoproteolytic cleavage, appears to require sequence specificity. Endoproteases specific for several recurrent amino acid sequence motifs identified in propeptide and prohormone polypeptides have been isolated and their substrate recognition sites explored. [Checler, et al., "Purification and characterization of a novel neurotensin-degrading peptidase from rat brain synaptic membranes," *J. Biol. Chem.* 261, 11274–11281 (1986); Clamagirand, et al., "Partial purification and functional properties of an endoprotease from bovine neurosecretory granules cleaving proocytocin/neurophysin peptides at the basic amino acid doublet," *Biochem.* 26, 6018–6023 (1987); Gluschankof, et al., "Role of peptide substrate structure in the selective processing of peptide prohormones at basic amino acid pairs by endoproteases," *FEBS Lett.* 234, 149–152 (1988)] Examples include endopeptidases specific for paired basic residues (commonly Lys-Arg or Arg-Arg), and cleavage sites characterized by a single proline. Monobasic residue recognition sites have also been found to attract specific proteolytic enzymes which hydrolyze peptide bonds either on the amino or carboxyl terminal side of a single arginine or lysine.

Physiological propeptides and prohormones often contain multiple cleavage sites, as well as amino acid sequences that comprise the recognition site yet do not undergo hydrolysis. One aspect of the putative sequence-specific endopeptidases is their ability to hydrolyze selected peptide bonds while leaving other consensus sites uncleaved. Furthermore, tissue-specific processing events demonstrate the ability of endoproteases to attack particular peptide bonds in one tissue but not others. [Loh, et al., "Proteolysis in neuropeptide processing and other neural functions," *Annu. Rev. Neuro.* 7, 189–222 (1984)] Clearly, additional parameters determine substrate recognition by endopeptidases, and most investigators concede that higher order structure must play a critical role.

In many experimental systems designed to study proteolytic processing, primary sequence simply cannot account for the selectivity of peptide bonds hydrolyzed by a given enzyme. For this reason, a number of reports documenting endoprotease substrate specificity acknowledge an apparent role played by secondary structure. [Beinfeld, et al., "Characterization of an endoprotease from rat small intestinal mucosal secretory granules which generates somatostatin-28 from prosomatostatin by cleavage after a single arginine residue," *J. Biol. Chem.* 264, 4460–4465 (1989), Gluschankof et al., supra (1988)] More recently, the structural features which govern peptide processing have been examined by assaying shortened synthetic analogues or precursor polypeptides modified by site-directed mutagenesis of cDNAs. [Brakch, et al., "Processing endoprotease recognizes a structural feature at the cleavage site of peptide prohormones," *J. Biol. Chem.* 264, 15912–15916 (1989); Docherty, et al., "Proinsulin endopeptidase substrate specificities defined by site-directed mutagenesis of proinsulin," *J. Biol. Chem.* 264, 18335–18339 (1989); Gomez, et al., "Site-specific mutagenesis identifies amino acid residues critical in prohormone processing," *EMBO J.* 8, 2911–2916 (1989); and Thorne, et al., "An in vivo characterization of the cleavage site specificity of the insulin cell prohormone processing enzymes," *J. Biol. Chem.* 265, 8436–8443 (1990)] Studies of this nature usually succeed only in identifying a specific residue at or nearby a cleavage site that influences substrate susceptibility, and the contribution made by the amino acid to the overall structure are of the full length substrate are not assessed.

A statistical analysis that revealed the high probability of β-turns at cleavage sites characterized by dibasic residues served to direct new attention to this particular structural motif. [Rholam, et al., "Precursors for peptide hormones share common secondary structures forming features at the proteolytic processing sites," *FEBS Lett.* 207, 1–6 (1986)] This observation has been directly challenged by the introduction or deletion of residues believed to influence the adoption of such a conformation at a cleavage site within synthetic substrates. [Brakch et al., supra 1989; Gomez et al., supra 1989] Most recently a computer algorithm designed to predict the occurrence of "omega loops" (long unstructured loops) at known prohormone dibasic cleavage sites indicated that hydrolyzed bonds may indeed be associated with this conformational motic as well. [Bek, et al., "Prohormonal cleavage sites are associated with omega loops," *Biochem.* 29, 178–183 (1990)] However, the structural contributions made by the remaining regions of the polypeptide are virtually ignored, and may remain untested due to the difficulties encountered in manipulating large polypeptides.

One exemplary model of sequence-independent processing is the action of peptidases involved in the cleavage of signal peptides of secreted proteins and the leader sequences which specify the targeting of mitochondrial proteins. Comprehensive studies by von Heijne and other investigators have established the role played by particular residues positioned nearby the cleavage site in governing recognition by these endopeptidases. [von Heijne, et al., "Patterns of amino acids near signal-sequence cleavage sites," *Eur. J. Biochem.* 133, 17–21 (1983); Duffaud, et al., "Signal peptidases recognize a structural feature at the cleavage site of secretory proteins," *J. Biol. Chem* 263, 10224–10228 (1988); and Folz, et al., "Substrate specificity of eucaryotic signal peptidase," *J. Biol. Chem.* 263, 2070–2078 (1988)] However, amino acids far upstream the cleavage site both within the hydrophobic core domain and the positively charged amino terminal region characteristic of signal peptides of secreted proteins have been found to profoundly influence processing as well. Amino acid substitutions that distort the alpha-helical potential of pre-proparathyroid hormone signal peptide or place hydrophilic residues into the conserved hydrophobic domain yield poor substrates for the cleavage reaction catalyzed by the eukaryotic signal peptidase. [Caulfield, et al., "Synthetic substrate for eucaryotic signal peptidase," *J. Biol. Chem.* 264, 15813–15817 (1989)]

Similarly, deletion of four residues from the amino terminus of yeast cytochrome oxidase subunit IV comprising the mitochondrial targeting signal served to prevent cleavage at the wildtype site twenty-five amino acids downstream. [Hurt, et al., "Amino-terminal deletions in the presequence of an imported mitochondrial protein block the targeting function and proteolytic cleavage of the presequence at the carboxy terminus," *J. Biol. Chem.* 262, 1420–1424 (1987)]

Magainins, first isolated as antibiotics, comprise a family of at least a dozen basic, ionophoric peptides and represents a model system for the study of vertebrate neuropeptides and hormones. [Zasloff, et al., "Antimicrobial activity of synthetic magainin peptides and several analogues," *Proc. Natl. Acad. Sci. USA* 85, 910–913 (1988); and Bevins, et al., "Peptides from frog skin," *Annu. Rev. Biochem.* 59, 395–414 (1990)] The magainin peptides are produced in the granular gland, specialized secretory cells that store large amounts of biologically active peptides and neurotransmitters. The granular glands are present in amphibian skin and stomach and release their contents in a holocrine fashion upon stress or injury. These structures are believed to serve physiological roles in defense against macroscopic predators and in microbial control following wounding. Strikingly, most hormones and many of the processing enzymes involved in their biosynthesis, stored in the anuran granular gland, have been found in the central nervous system and diffuse peripheral nervous system of mammals. [Bevins et al., supra (1990)]

The magainin peptides are synthesized from polyproteins, from which, in several cases, both antibiotic and hormonally active peptides are liberated. [Sures, et al., "Xenopsin: the neurotensin-like octapeptide from Xenopus skin at the carboxy terminus of its precursor," *Proc. Natl. Acad. Sci. USA* 81, 380–384 (1984); Richter, et al., "Sequence of preprocaerulein cDNAs cloned from skin of *Xenopus laevis*," *J. Biol. Chem.* 261, 3676–3680 (1986); and Poulter, et al., "Levitide, a neurohormone-like peptide from the skin of *Xenopus laevis*," *J. Biol. Chem.* 263, 3279–3283 (1988)] The primary sequences bracketing the biologically active peptides represent putative hormone processing sites, and these include the dibasic and monobasic cleavage sites characteristic of processing signals on mammalian neuropeptide precursors. The peptides contained within the granular gland are stored within secretory vesicles as processed, active species suggesting that initial proteolytic events occur prior to secretion. [Gibson, et al, "Novel peptide fragments originating from PGLa and the caerulein and xenopsin precursors from *Xenopus laevis*," *J. Biol Chem.* 261, 5341–5349 (1986)]

After peptides are discharged from the granular glands, they undergo further proteolysis, resulting in half-peptide fragments. Gibson et al., "Biosynthesis and degradation of peptides derived from *Xenopus laevis* prohormones," (1986); Giovannini, et al., supra (1987)] The half-peptide products have been fully characterized by extensive mass-spectroscopic analyses. Because the processed peptides no longer retain antibiotic activity, the processing reaction represents an inactivation step. At the same time, however, the half molecules accumulate in the secretion and several have been shown to undergo subsequent carboxyl-terminal amidation, a modification common to many hormones. [Gibson, et al., supra (1986)] Thus, although endoproteolysis inactivates the antibiotic activity of the magainin peptides, it may serve to liberate new hormones as well.

The secretions of *Xenopus laevis* has been used as a model to investigate, in vivo, the mechanisms of processing and biosynthesis of the peptide precursors and the fate of the peptides after secretion. [Giovannini et al., supra (1987)] Proteolysis of the larger primary products from *X. laevis* was reported to take place after secretion and possibly brought about by a cytoplasmic enzyme very specific for Xaa-Lys bonds, where Xaa is Ala, Lys, Leu or Gly. In the alternative it was postulated that proteolysis could be by an enzyme packed with the vesicles, but inactive before secretion. It was noted that xenopsin, containing the sequence Gly-Lys, was not cleaved under the reported conditions and it was suggested that the secondary structure of the peptides or neighboring amino acids play an important role in determining the accessibility of the site to proteolysis.

A wide variety of proteins can be and are currently produced by synthetic means such as recombinant technology. The generation of these recombinant proteins by host cells often result in proteins that require further processing to yield the mature functional protein desired. In attempts to mimic the natural processing of the recombinantly produced protein, the expressed proteins have been exposed to proteolytic enzymes. Generally, proteolytic enzymes are site specific and can result in multiple cleavages where the peptide of interest contains several sites recognized by the enzyme. In the field of synthetic protein production there is a need for enzymes with more sophisticated substrate specificity that can be utilized to process proteins such as the type that possess multiple recognition sites for traditional site specific enzymes.

SUMMARY OF THE INVENTION

There is provided by the invention a novel composition comprising, in at least partially purified form, an endopeptidase endogenous to biological cells such as from the skin of *Xenopus laevis*. The endopeptidase is characterized by having a molecular weight of about 110,000 daltons as measured by SDS PAGE; enzyme activity being substantially insensitive to PMSF, TPCK, E-64, leupeptin, bacitracin, phosphoramidon and pepstatin; enzyme activity being at least partially inhibited by EDTA and 1,10-phenanthroline; and being capable of cleaving at least some peptide substrates comprising an alpha helical structural of at least about twelve to fourteen amino acids wherein said helix has a hydrophobic face and a hydrophilic face, said cleavage occuring amino terminal to a lysine or arginine residue on the hydrophilic face said lysine or arginine positioned within the context of at least four nonpolar amino acids substantially aligned along the hydrophobic face of the helix. Further provided by the invention is a novel isolated DNA sequence encoding the endopeptidase of this invention.

Further provided by the invention is a novel recombinant expression vector containing a DNA sequence encoding the endopeptidase of the invention wherein the vector is capable of expressing the endopeptidase in a host cell.

Further provided by the invention is a novel host cell transformed with the DNA encoding the endopeptidase of the invention or a portion thereof sufficient for the expression of endopeptidase by said host cell.

Further provided by the invention is a novel method of producing the endopeptidase of the invention, and the endopeptidase produced thereby, which comprises culturing recombinant host cells transformed with a DNA sequence coding for said endopeptidase operably linked to appropriate regulatory control sequences which sequences are capable of effecting the expression of said coding sequence in said transformed cells and recovering said expressed endopeptidase.

Further provided by the invention is a novel method of hydrolyzing peptides substrates comprising the steps of providing a peptide substrate comprising an alpha helical structural of about twelve to fourteen amino acids wherein said helix has a hydrophobic face and a hydrophilic face and a lysine or arginine residue on the hydrophilic face positioned within the context of at least four nonpolar amino acids substantially aligned along the hydrophobic face of the helix; and contacting said peptide substrate with the endopeptidase of the invention under conditions sufficient to permit hydrolysis of the peptide substrate by the endopeptidase.

Further provided by the invention is a novel method of synthesizing larger peptides from a plurality of smaller peptides or amino acids comprising bringing said smaller peptides or amino acids in contact with a condesation catalytically effective amount of the endopeptidase of the invention under conditions conducive to synthesis of larger peptides from a plurality of smaller peptides or amino acids.

Surprisingly, the endopeptidase of this invention hydrolyzes peptides on the basis of secondary structure rather than primary amino acid sequence alone and therefor provides a useful tool in the field of peptide processing.

BRIEF DESCRIPTION OF THE DRAWINGS

FIG. 3. A Single Enzyme is Active Against Several Peptide Substrates (A) Silver-stained SDS-polyacrylamide gel of fractions 25–33 recovered from a 15–30% glycerol gradient fractionation of enzyme activity. The arrow indicates the opposite direction of sedimentation.

Endoproteolytic cleavage of magainin 2-amide (B), PGLa (C) and xenopsin precursor fragment (XPF) (D) is detected by acid polyacrylamide gel electrophoresis followed by Coomassie Blue staining. The number denoting the glycerol gradient fraction at the bottom indicates the source of enzyme utilized for each individual assay monitored by acid gel electrophoresis. The arrows denote the migration of each full-length uncleaved peptide substrate, and the disappearance of that band in each gel indicates conversion to half-peptide products. In the case of both PGLa and XPF, cleavage serves to liberate amino-terminal half-peptides with no net electostatic charge thereby precluding their migration into the gel.

Figure 4A:
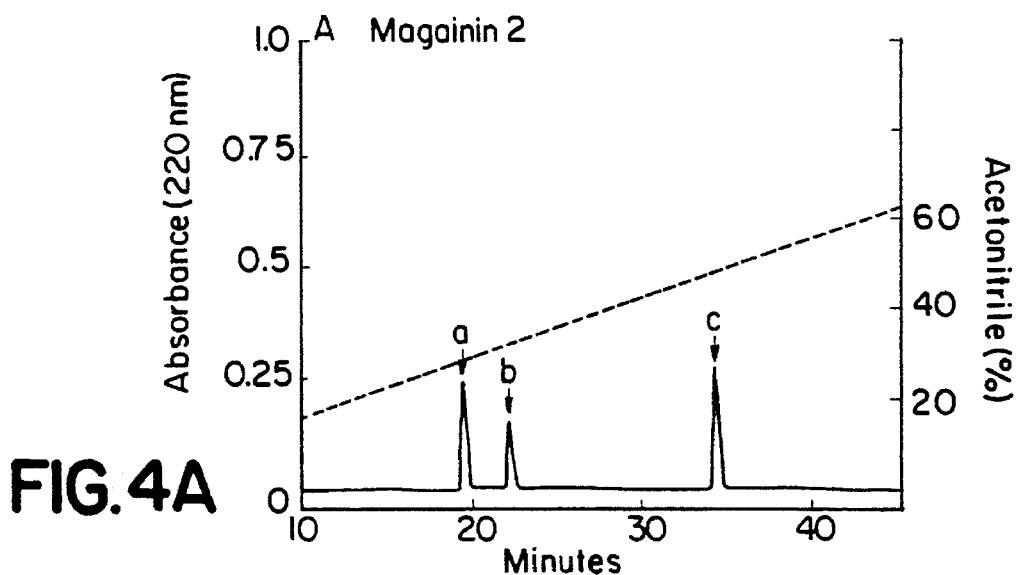
Figure 4B:
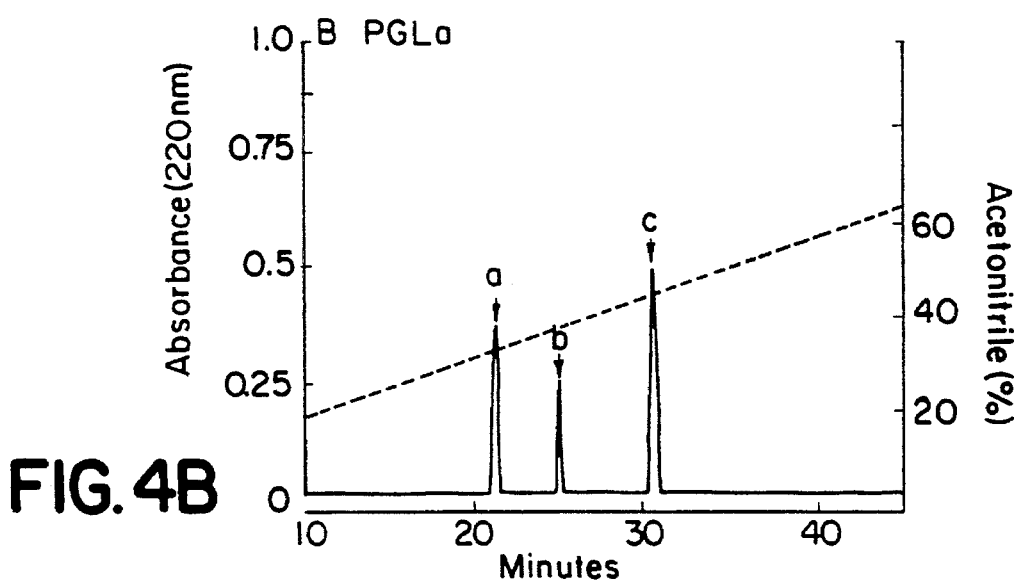
Figure 4C:
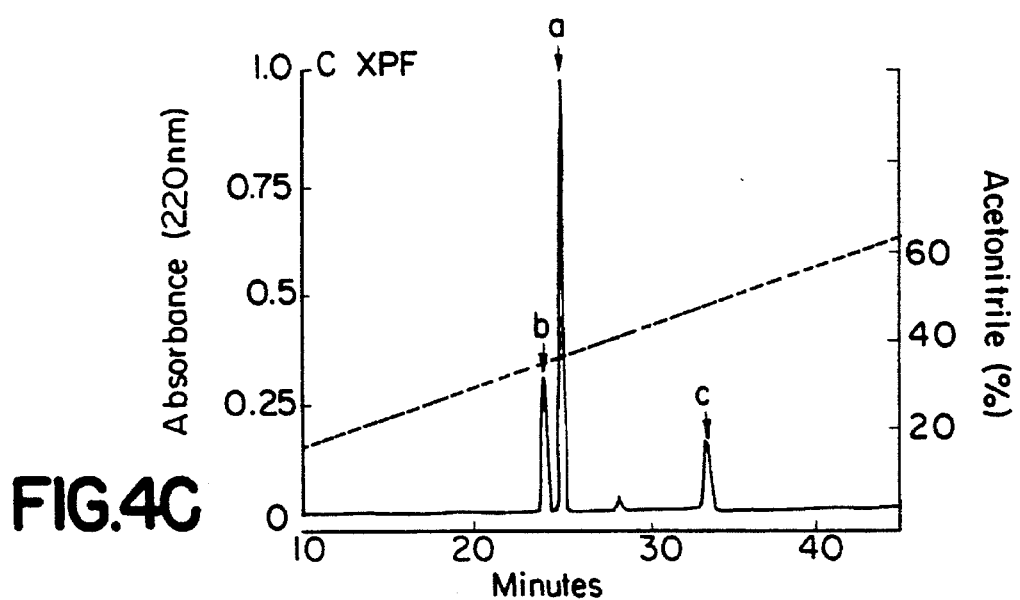

FIG. 4. The Enzyme is an Endopeptidase

Reversed-phase HPLC chromatographs of cleavage reactions utilizing one unit of enzyme activity. Standard 100 ul reactions analyzing cleavage against magainin 2-amide (A), PGLa (B) and XPF (C) were run and then subjected to HPLC. Peak a in each reaction was shown by subsequent amino acid analyses (described in Experimental Procedures) to represent the amino-terminal half peptide, peak b represents the carboxyl-terminal half peptide, and peak c represents the uncleaved full-length peptide substrate. Reversed-phase HPLC analysis was performed as described in Experimental Procedures.

Figure 5:
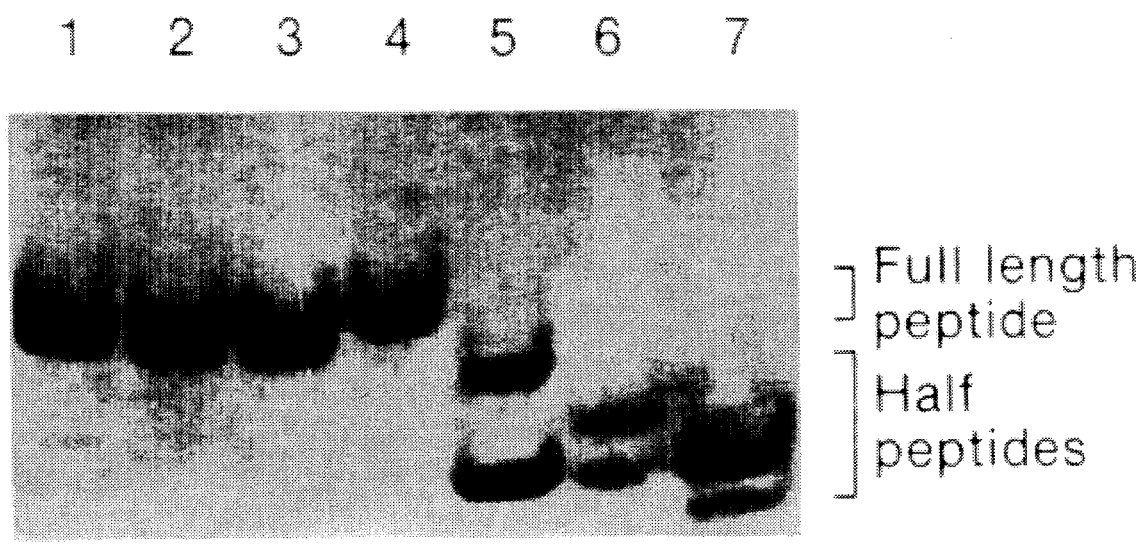

FIG. 5. Magainin 2 Amino-terminal Truncation Analogues Resist Endoproteolytic Attack Standard enzyme assays testing cleavage of magainin 2-amide amino and carboxyl-terminal truncation analogues were conducted and cleavage monitored by acid gel electrophoresis. (Deletion analogue (Des) Lanes 1–4 (Des-1 through Des-1–4 analogues) demonstrate the absence of any half-peptide products, while lanes 5–7 (Des-22–23, Des-20–23 and Des-18–23 respectively) reveal the liberation of half-peptide products as denoted. Acid gel electrophoresis was conducted as described in Experimental Procedures.

Figure 6:
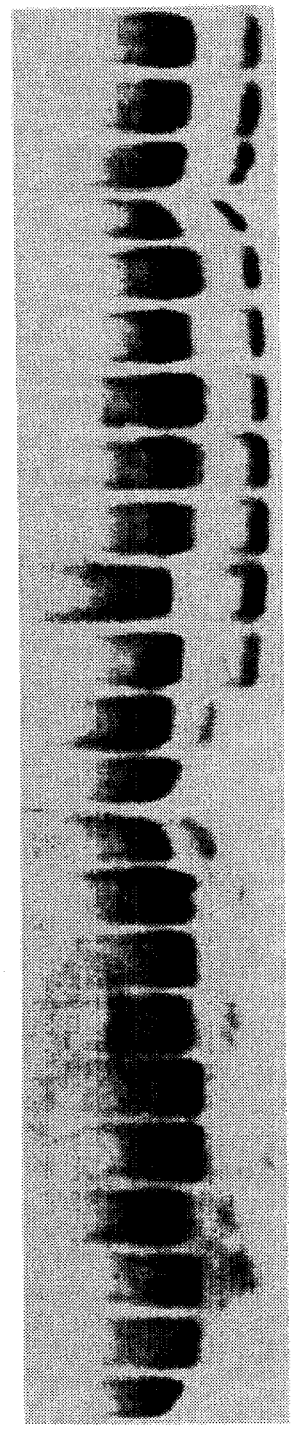
Figure 7A:
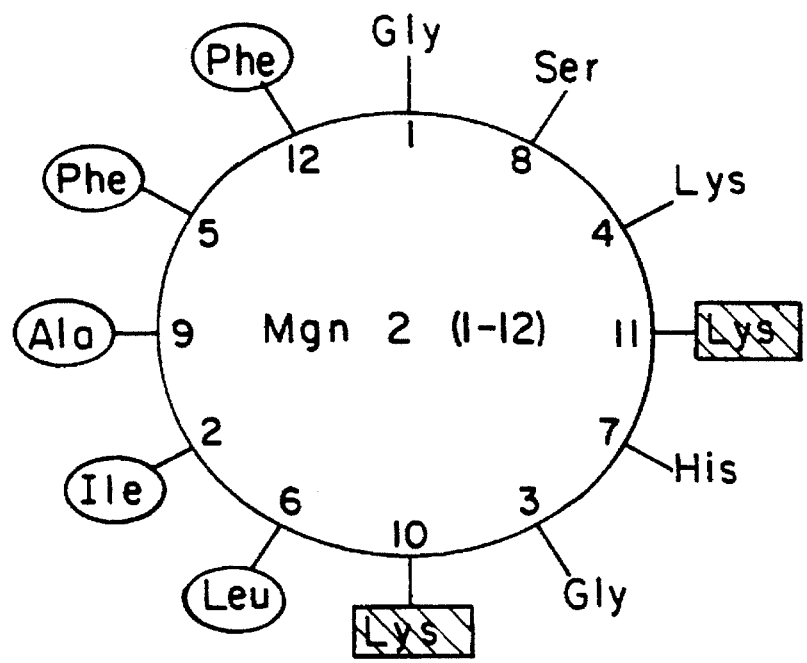
Figure 7B:
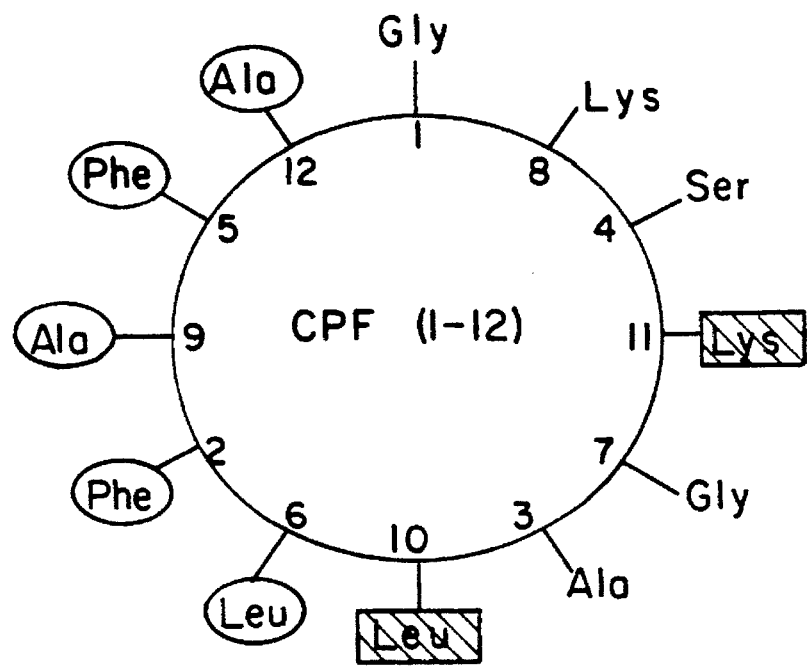
Figure 7C:
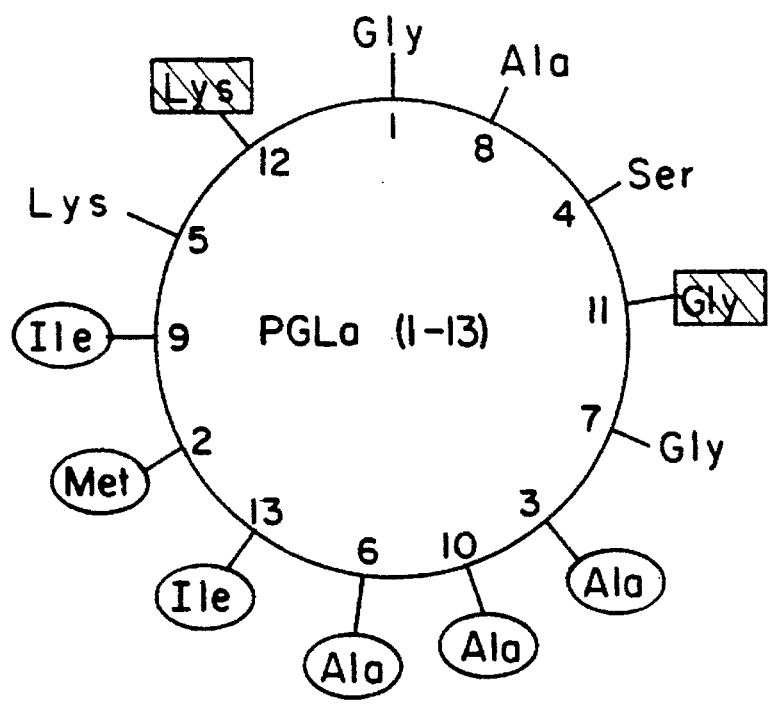
Figure 7D:
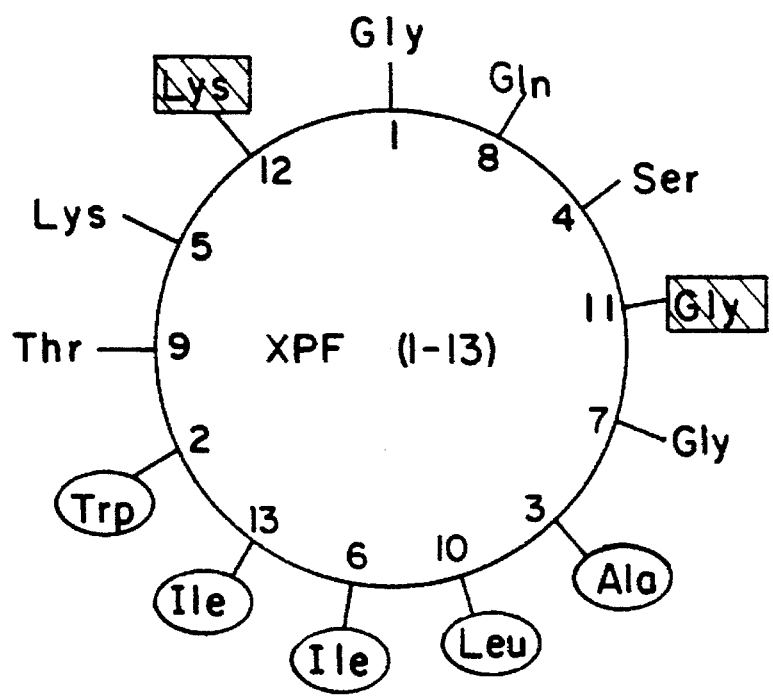

FIG. 6. Single Amino Acid Omissions in the Amino-terminal Half of Magainin 2 Result in Peptides that are Resistant to Endopeptidase Activity The single letter amino acid code below each lane in this acid acrylamide gel denotes the residue omitted from the synthetic magainin 2 analogue tested for cleavage by the endopeptidase in that reaction. Analogues susceptible to attack are revealed by the appearance of the N-terminal and C-terminal half-peptides as labelled on the right.

FIG. 7. The Natural Substrates Modelled as Helical Wheels

Helical wheels of each natural peptide substrate (residues 1–12 of magainin 2 and caerulein precursor fragment (CPF), residues 1–13 of PGLa and XPF) reveals structural similarities despite their variable amino acid sequences. Hydrophobic amino acids comprising the nonpolar face of each helix are circled, and the residues bracketing each cleavage site (located on the hydrophilic face) are shaded.

Figure 8A:
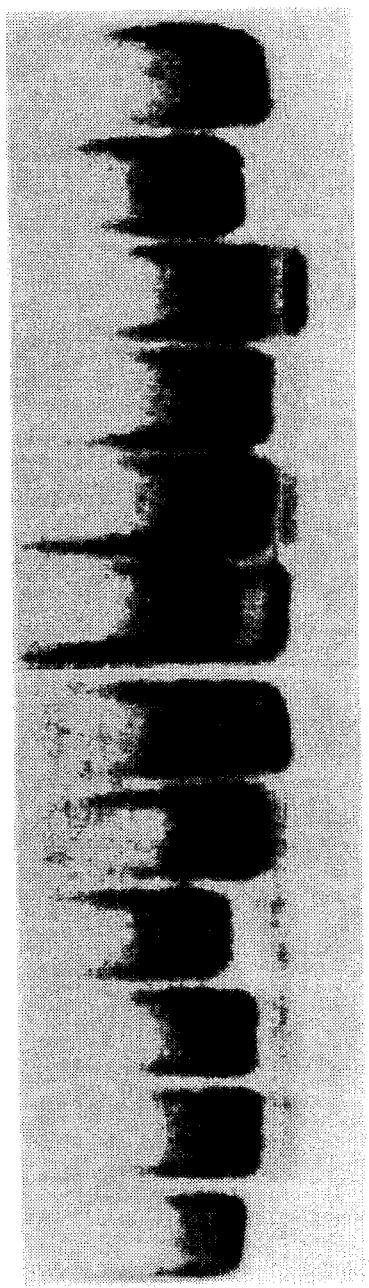
Figure 9A:
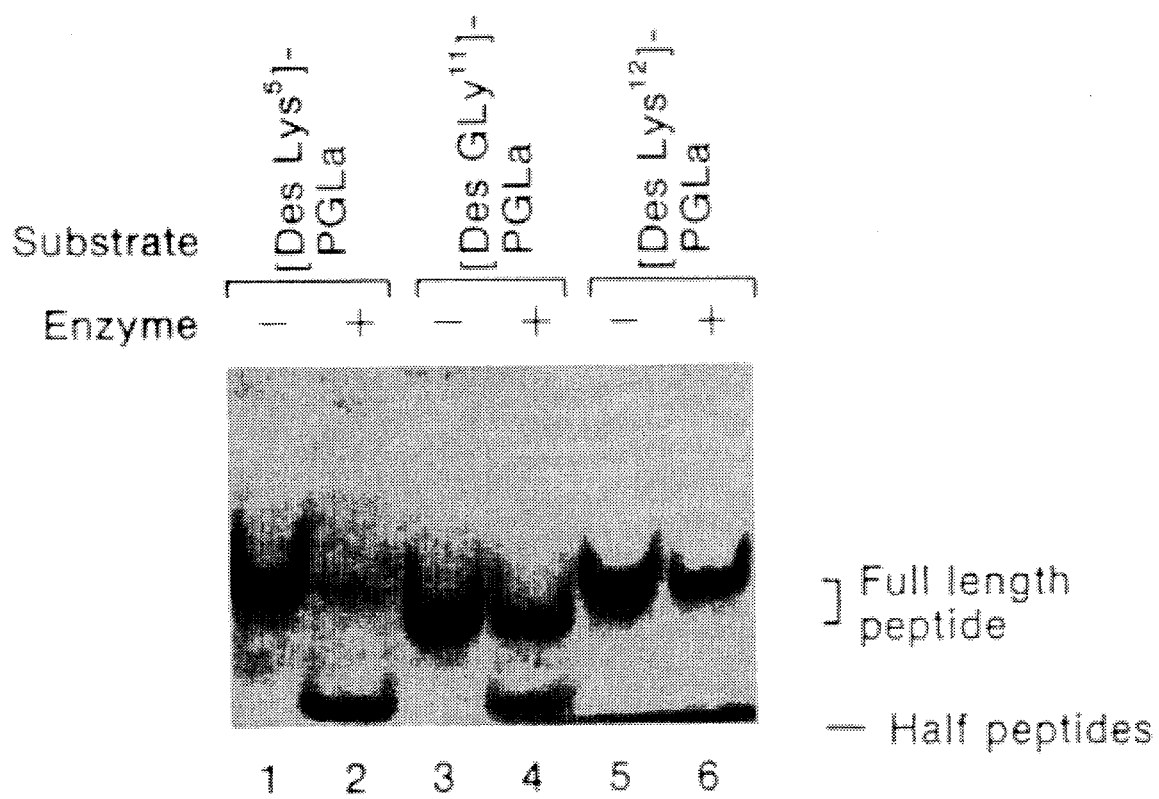
Figure 8B:
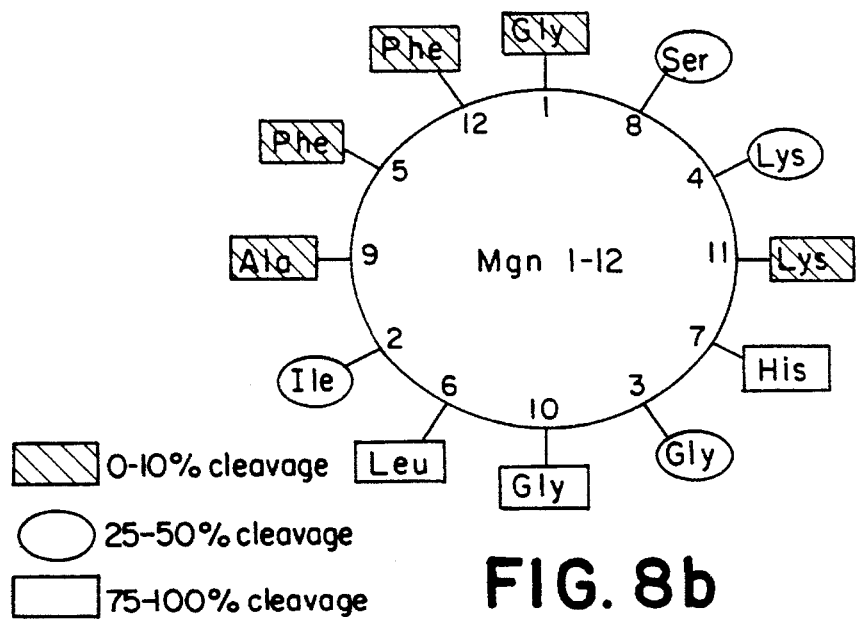
Figure 9B:
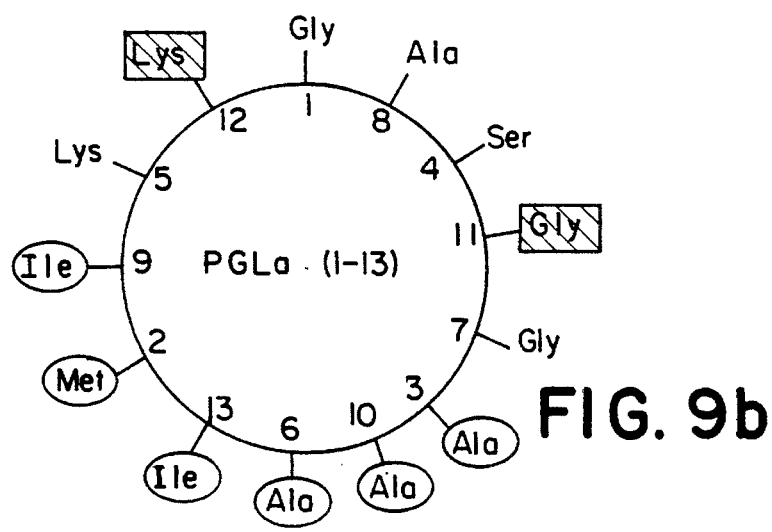
Figure 9C:
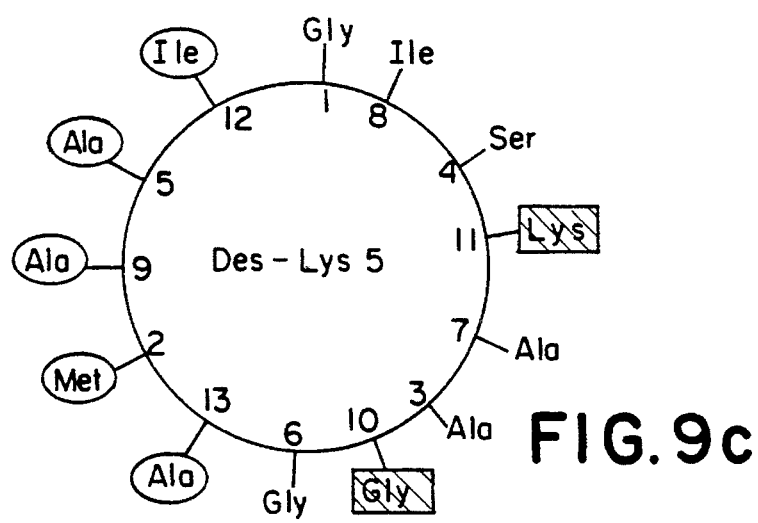
Figure 9D:
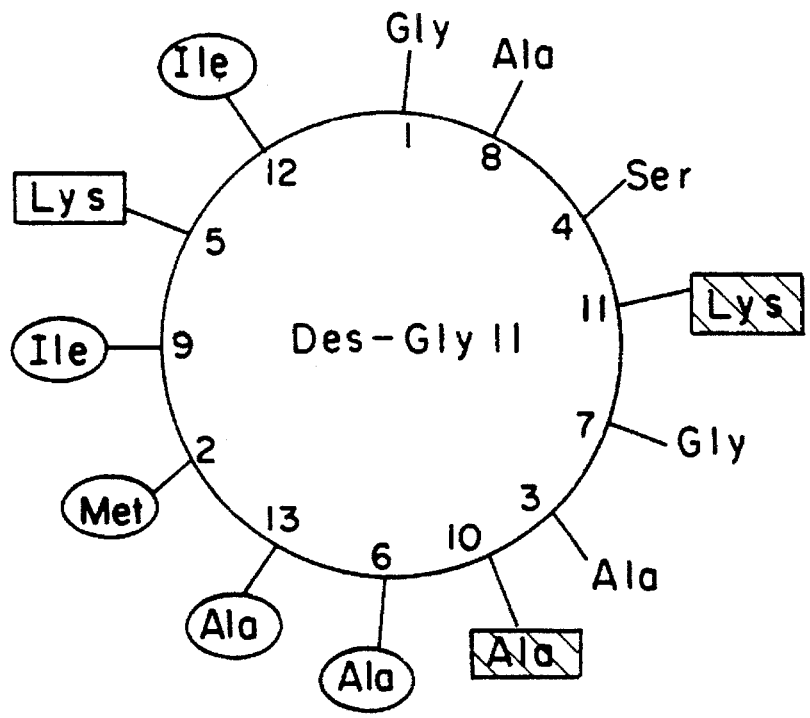
Figure 9E:
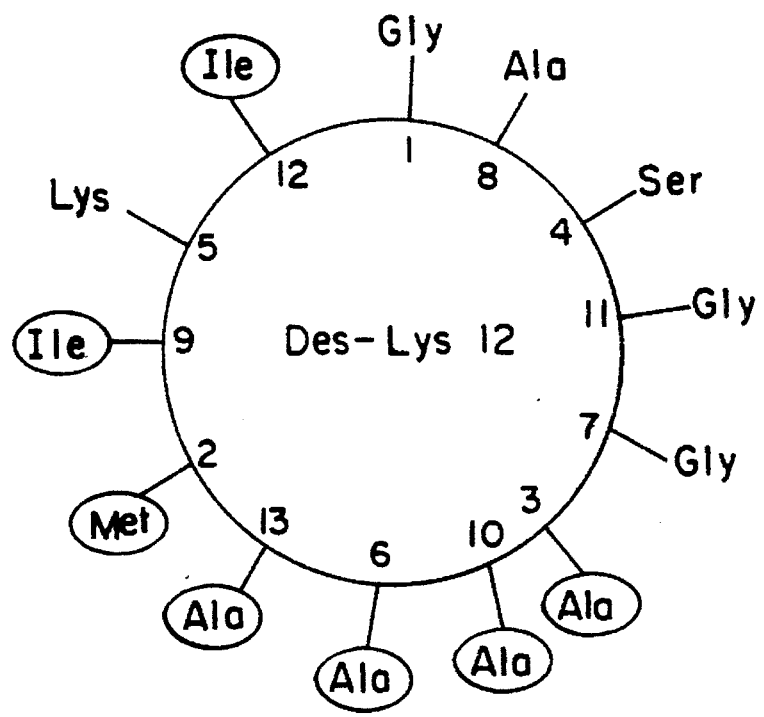

FIG. 8. Substrate Hydrophobicity is a Determinant of Recognition (A) Acid acrylamide gel of reactions utilizing glutamate substitution analogues. The single letter amino acid code below each lane represents the wildtype residue replaced with a glutamate in that analogue. Cleavage is detected in this acid acrylamide gel by the appearance of the amino-terminal half-peptide as labelled on the right.

(B) The results of glutamate substitutions as depicted on the magainin helical wheel are shown. Substitutions which resulted in 0 to 10% cleavage activity (relative to activity against native magainin 2) are shown as boxed, shaded residues. Substitions resulting in 25 to 50% cleavage are circled and substitutions resulting in 75 to 100% activity are boxed. Percent cleavage of each substitution analogue was determined visually from Coomassie Blue stained acid gels and are summarized from several independent experiments.

FIG. 9. Endopeptidase Activity Against PGLa Omission Analogues Supports the Deduced Structural Motif (A) Acid acrylamide gel demonstrating cleavage of Des-Lys5 and Des-Gly11 PGLa analogues. Lanes 1, 3 and 5 are reactions run in the absence of enzyme and serve as control lanes of uncleaved, full-length peptides. Lanes 2, 4 and 6 are reactions including enzyme, and cleavage is identified by the generation of the amino-terminal half-peptide.

(B) Helical wheel projections of native PGLa (1–13) and the three single residue omission analogues assayed for cleavage in (A). Hydrophobic amino acids constituting the nonpolar face of each potential alpha-helic are circled, the amino acids bracketing the scissile bond are shaded, and the displaced lysine believed to affect cleavage of the Des-Gly 11 analogue is enclosed in a square.

Figure 10:
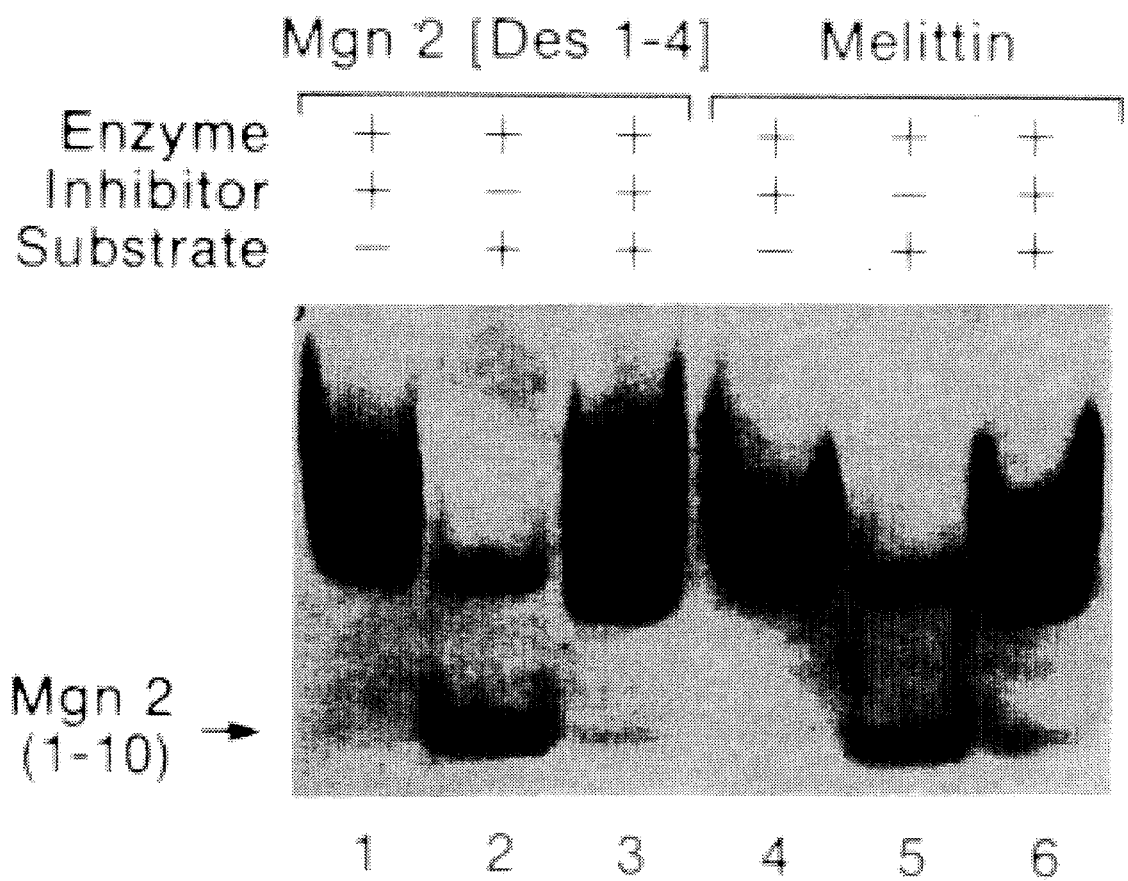

FIG. 10. Analysis of Peptides as Inhibitors of Endopeptidase Activity

Acid acrylamide gel of enzymatic assays designed to test ability of magainin 2 Des 1–4 analogue and melittin to inhibit endopeptidyl cleavage of native magainin 2-amide. Lanes 1 and 4 represent controls demonstrating that both potential inhibitors do not serve as substrates of the endopeptidase. Lanes 2 and 5 also serve as controls and demonstrate 100% cleavage of native magainin 2-amide in the absence of any inhibitors. Lanes 3 and 6 demonstrate the results of incubating enzyme with a tenfold excess of inhibitor prior to adding native substrate. Inhibition assays were conducted as described in Experimental Procedures.

FIG. 11. Summary of Peptides and Analogues Tested Against Endopeptidase

Arrows denote cleavage sites identified by reversed-phase HPLC and amino acid analyses as described in Experimental Procedures. Underlined residues denote cleavage sites identified by acid polyacrylamide gel electrophoresis. Amino acids omitted from peptide termini are represented as dashes (B), while residues internally omitted are denoted by a space in the full-length sequence (C and E). Substituted amino acids are represented as highlighted single letters (D and F). The column on the right summarizes the relative cleavage of each peptide analogue relative to endopeptidase activity against native magainin 2-amide. Four plus signs represent wildtype levels of cleavage, while a minus sign indicates no cleavage. All determinations of relative cleavage were made by visualizing acid acrylamide gels stained in Coomassie Blue as described in Experimental Procedures. All peptides listed are synthesized as terminal carboxylamidated molecules with the exception of those denoted by an asterisk.

DETAILED DESCRIPTION OF THE INVENTION

A novel endopeptidase, endogenous to biological cells such as cells from the skin of *Xenopus laevis* has been purified to homogeneity and is provided by this invention. This approximately 110 kDa, protein is believed to function as a monomer and appears to be a metallopeptidase based on its inhibition by metal chelating agents. Through the utilization of numerous synthetic peptide analogues, the structural determinants of substrate specificity for the endopeptidase of this invention have been identified. The endopeptidase of this invention is believed to recognize a peptide substrate with an amphipathic, alpha-helical domain comprised of (1) at least twelve amino acids, (2) a hydrophobic face and (3) a lysine or arginine residue on the hydrophilic face positioned within the context of at least four nonpolar amino acids aligned along the hydrophobic face.

"Alpha-helical" as used herein refers to the arrangement of protein molecules in which polypeptide chains of proteins spiral right-handedly to form helices. As stated above, it is believed a feature of endopeptidase activity is substrate hydrophobicity. More specifically, it is believed one face of the amphipathic, alpha helix motif must be hydrophobic in order to be recognized as an optimal substrate by the novel endopeptidase. While not wishing to be bound by any particular theory, it is envisioned that a hydrophobic interaction between the enzyme of this invention and substrate facilitates the initial binding reaction preceding hydrolysis of the protein.

The endopeptidase of this invention is present in the skin of *X. laevis* in relatively large quantities and can be isolated in at least partially purified form by conventional chromatography methods. Furthermore, it is believed that the endopeptidase of the invention can be obtained as a naturally occuring endopeptidase from other biological cells where peptide substrates with an amphipathic, alpha-helical domain comprised of (1) at least twelve amino acids, (2) a hydrophobic face and (3) a lysine or arginine residue on the hydrophilic face positioned within the context of at least four nonpolar amino acids substantially aligned along the hydrophobic face which substrates are hydrolyzed to smaller fragments.

If desired, the amino acid and DNA sequence of the endopeptidase can be readily determined by methods known to those in the art. Briefly, to obtain the amino acid sequence, a DNA molecule is synthesized which encodes a partial amino acid sequence of the enzyme or which represents the complementary DNA strand to such a DNA molecule which encodes a partial amino acid sequence. This synthetic DNA molecule may then be used to probe for DNA sequence homology in DNA sequences derived from the genomic DNA of the organism or derived from cDNA copies of mRNA molecules isolated from the organism. Generally, DNA molecules of fifteen (15) nucleotides or more are required for unique identification of an homologous DNA. The number of different DNA molecules which can encode the amino acid sequence may be very large since each amino acid may be encoded for by up to six (6) unique trinucleotide DNA sequences or codons. Therefore, it is impractical to test all possible synthetic DNA probes individually and pools of several such DNA molecules can be used concomitantly as probes. The production of such pools which are referred to as "degenerate" probes is well known in the art. While only one DNA molecule in the probe mixture will have an exact sequence homology to the gene of interest, several of the synthetic DNA molecules in the pool may be capable of uniquely identifying the gene since only a high degree of homology is required.

One technique to identify a gene sequence employs the Polymerase Chain Reaction (PCR). See e.g., U.S. Pat. Nos. 4,683,195 and 4,683,202 which patents are incorporated by reference as if fully set forth herein. Essentially PCR allows the production of a selected DNA sequence when the two terminal portions of the sequence are known. Primers, or oligonucleotide probes, are obtained which correspond to each end of the sequence of interest. Using PCR, the central portion of the DNA sequence is then synthetically produced.

In one such method of employing PCR to obtain the gene, RNA is isolated from the organism and purified. A deoxythymidylate-tailed oligonucleotide is then used as a primer in order to reverse transcribe the RNA into cDNA. A synthetic DNA molecule or mixture of synthetic DNA molecules as in the degenerate probe described above is then prepared which can encode the amino-terminal amino acid sequence of the enzyme as previously determined. This DNA mixture is used together with the deoxythymidylate-tailed oligonucleotide to prime a PCR reaction. Because the synthetic DNA mixture used to prime the PCR reaction is specific to the desired mRNA sequence, only the desired cDNA will be effectively amplified. The resultant product represents an amplified cDNA which can be ligated to any of a number of known cloning vectors.

Finally, the produced cDNA sequence can be cloned into an appropriate vector using conventional techniques, analyzed and the nucleotide base sequence determined. A direct amino acid translation of these PCR products will reveal that they corresponded to the complete coding sequence for the enzyme.

In addition to obtaining the enzyme directly from biological cells such as frog skin, it is believed the enzyme can be efficiently prepared using any of numerous well known recombinant techniques. Briefly, most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

The most commonly used procaryotes system for the production of recombinant proteins remains E. coli, however, other microbial strains may also be used, such as bacilli, for example Bacillus subtilis, various species of Pseudomonas, or other bacterial strains. In such procaryotic systems, plasmid vectors which contain replication sites and control sequences derived from a species compatible with the host are used. Commonly used procaryotic control sequences include promoters for transcription initiation, optionally with an operator, along with ribosome binding site sequences.

A wide variety of eucaryotic hosts are also now available for production of recombinant foreign proteins. As in bacteria, eucaryotic hosts may be transformed with expression systems which produce the desired protein directly, but more commonly, signal sequences are provided to effect the secretion of the protein. Eucaryotic systems have the additional advantage that they are able to process introns which may occur in the genomic sequences encoding proteins of higher organisms. Eucaryotic systems also provide a variety of processing mechanisms which result in, for example, glycosylation, oxidation or derivatization of certain amino acid residues, conformational control, and so forth.

Commonly used eucaryotic systems include yeast, insect cells, mammalian cells, avian cells, and cells of higher plants. The list is not exhaustive. Suitable promoters are available which are compatible and operable for use in each of these host types as well as are termination sequences and enhancers, as e.g. the baculovirus polyhedrin promoter. As above, promoters can be either constitutive or inducible. For example, in mammalian systems, the MTII promoter can be induced by the addition of heavy metal ions.

The particulars for the construction of expression systems suitable for desired hosts are known to those in the art. For recombinant production of the protein, the DNA encoding it is suitably ligated into the expression system of choice, and the system is then transformed into the compatible host cell which is then cultured and maintained under conditions wherein expression of the foreign gene takes place. The endopeptidase of this invention thusly produced is recovered from the culture, either by lysing the cells or from the culture medium as appropriate and known to those in the art.

Correct ligations for plasmid construction can be confirmed by first transforming a suitable host with the ligation mixture. Successful transformants are selected by ampicillin, tetracycline or other antibiotic resistance or using other markers depending on the mode of plasmid construction, as is understood in the art.

The endopeptidase of this invention is believed to be valuable in the processing of peptides, e.g., peptides that have been recombinantly produced and require specific hydrolysis to generate the protein of interest. One skilled in the art will recognize that peptides can be processed in a variety of ways, e.g., directly by contact with the endopeptidase under conditions conducive to hydrolysis. Additionally, it is believed that the DNA for the enzyme of this invention can be ligated to the DNA of the protein(s) that require processing so that upon expression of the chimeric gene, the peptides are processed automatically.

Further provided by the invention is a novel method of synthesizing larger peptides from a plurality of smaller peptides or amino acids comprising bringing said smaller peptides or amino acids in contact with a condensation catalytically effective amount of the endopeptidase of the invention under conditions conducive to synthesis of larger peptides from a plurality of smaller peptides or amino acids. Those skilled in the art can readily determine a condensation catalytically effective amount of the enzyme to be used. A condensation catalytically effective amount of enzyme is that amount sufficient to result in the condensation (synthesis of larger peptides) of at least some smaller peptides of amino acids.

Thus, the endopeptidase of this invention is believed useful as a condensation catalyst in the synthesis of larger peptides from a plurality of smaller peptides. The use of certain proteolytic enzymes as condensation catalysts has been described. See e.g. U.S. Pat. No. 5,002,871 which patent is incorporated by reference as if fully set forth herein and V. Kasche, "Protease and peptide synthesis," *Proteolytic enzymes a practical approach*, pp. 125–145 ed. R. J. Baynum and J. S. Bond, IRL Press (1989).

EXPERIMENTAL PROCEDURES

MATERIALS—*Xenopus laevis* frogs were purchased from Nasco (Fort Atkinson, Wis.). Ammonium sulfate was purchased from Bethesda Research Laboratories, glycerol, ammonium acetate and Nonidet P-40 were purchased from Sigma, St. Louis, Mo. Acrylamide was purchased from Boehringer Mannheim, Indiannapolis, Ind. Phenanthroline, leupeptin, pepstatin, PMSF, TPCK, E-64, phosphoramidon and mellitin were purchased from either Sigma or Boehringer Mannheim. Mastoparan was purchased from Peninsula Laboratories, Inc., Belmont, Calif.

PEPTIDE SYNTHESIS—Magainins 1 and 2, PGLa, XPF, CPF (FIG. 11A) and all derivatives of such peptides were synthesized by the solid phase procedure as previously described. Zasloff, et al. supra (1988).

ENZYME ASSAYS—Activity was monitored by incubating 0.1–10 µl of each chromatographic fraction with 50 µg of magainin 2-amide substrate in a total volume of 100 µl for one hour at room temperature. Reaction buffer consisted of 20 mM Na phosphate, 50 mM NaCl final concentration. After quenching the reaction with 0.5 volume of glacial acetic acid, a 15 µl aliquot of each reaction was analyzed by acidic gel electrophoresis. One unit of enzyme activity is defined as the amount of enzyme required to convert 25 µg of magainin 2-amide substrate into half-peptide products under the above conditions.

Substrate specificity analyses were carried out as described above except that 50 µg of each substrate analogue under investigation was substituted for magainin 2-amide in the incubation at the same concentration.

Inhibitor studies were conducted in the same fashion; the only difference involved first incubating the enzyme with each inhibitor tested at a particular concentration in the absence of any substrate for one hour at room temperature. Substrate was then added to the reaction and allowed to incubate for an additional hour at room temperature.

ACIDIC GEL ELECTROPHORESIS—Acidic gels (pH 4) were prepared and run as originally described (Gabriel, 1971) with several modifications. The gel solution consisted of a final concentration of 15% (v/v) acrylamide (acrylamide:bisacrylamide/37.5:1), 88 mM KOH, 3% (v/v) glacial acetic acid, 0.75% (v/v) tetraethylene methylene diamine (Temed), 0.375% ammonium persulfate (30 mg/ml). Before loading samples, 0.5 volume of glacial acetic acid was added, as well as 0.5 volume of 0.1% Pyronin Y loading dye. MINI PROTEAN gel apparatus (Biorad, Richmond, Calif.) were used and gels electrophoresed at 200 volts in running buffer containing 0.035M β-alanine and glacial acetic acid (2.45 ml/l), pH 4.0. Gels were stained in 0.1% (w/v) Coomassie Brilliant Blue R-250 (Sigma), 50% methanol, 50% water and destained in distilled water.

SODIUM DODECYL SULFATE POLYACRYLAMIDE GEL ELECTROPHORESIS—SDS PAGE was carried out following the method of Laemmli. Laemmli, U. K., "Cleavage of the structural proteins during the assembly of the head of bacteriophage T4," *Nature* 227, 680–685 (1970). High moecular weight standards were purchased from Biorad.

HPLC and AMINO ACID ANALYSES—Enzyme reactions subjected to these analyses were first terminated in 1% trifluoroacetic acid (TFA) to a final concentration of 0.1% TFA. 100 µl reactions were injected into a Beckman HPLC System Gold instrument and run on a C18 reversed phase column (4.6×220 mm, Aquapore OD-300, Applied Biosystems, Foster City, Calif.). A linear gradient of 30–70%, buffer A=0.1% TFA in H20, buffer B=0.08% TFA in acetonitrile, was established over a period of 45 minutes at a flow rate of 1 ml/min. Fractions containing peptide were lyophilized and resuspended in HPLC grade water. Portions of the resuspended sample were injected into an amino acid analyzer with automated hydrolysis (model 420/130, Applied Biosystems, Foster City, Calif.), and numerical calculations for specific amino acids were determined using an Applied Biosystems 920A data analysis module.

PROTEIN CONCENTRATION—Protein concentration was determined either by the method of Bradford (Biorad) or by the Pierce BCA assay using bovine serum albumin as a standard.

PURIFICATION—Approximately 50 mg total of dorsal and ventral Xenopus skin were dissected from the anesthetized animals, weighed and homogenized by a Polytron in ten volumes of 50 mM NH$_4$Acetate, 15% (v/v) glycerol, pH 7.0 (buffer A). After centrifugation at 10 rpm for 40 minutes a5 4° C., the supernatant was collected and saturated with ammonium sulfate to 30%. Following precipitation and centrifugation, the supernatant was saturated to 60% with ammonium sulfate and again precipitated. The pellet was resuspended in 20 ml of buffer A and dialyzed extensively against the same buffer.

The dialyzed sample was then subjected to recycling free-flow isoelectric focusing on a RF-3 instrument (Protein Technologies, Inc., Tucson, Ark.) prefocused in 1% (w/v) pH 4–6 ampholytes, 15% (v/v) glycerol and 0.1% (v/v) Triton X-100 for approximately 60 minutes at 1500 volts. The sample was focused for 120 minutes at a temperature of 7°–10° C. 2.5 ml fractions were collected and assayed for enzymatic activity.

All subsequent steps were carried out at 40° C. Active fractions were pooled and concentrated by Centricon 30 (Amicon, Beverly, Mass.) tubes and loaded onto a Sephacryl S-300 HR (Pharmacia, Piscataway, N.J.) column (2.5×22 cm) equilibrated in 50 mM NH$_4$ Acetate, 0.1% (v/v) Nonidet P-40 (Sigma), pH 7 (buffer B). The sample was washed and eluted in buffer B at a flow rate of 0.5 ml/min. 1.5 ml fractions were collected and protein detected by UV absorbance at 280 nm.

A subset of active fractions was again pooled after analysis by both enzymatic activity and denaturing gel electrophoresis. A Biogel HPT hydroxylapaptite (Biorad) column (1×5 cm) equilibrated in 50 mM Na phosphate, 0.1% (v/v) NP-40, pH 7 was next loaded with the pooled sample and washed with ten column volumes of the same buffer. Elution of the enzyme was achieved with a 25 ml linear gradient from 50 mM to 500 mM NaHPO4, 0.1% (v/v) NP-40 at a flow rate of 0.1 ml/min. After analyzing the 0.5 ml fractions for enzyme activity, active fractions were pooled and concentrated by ultrafiltration.

12 ml glycerol gradients consisting of 15–30% glycerol in 50 mM NH$_4$Ac were prepared in siliconized polyallomer (14×95 mm) tubes (Beckman). Pooled, concentrated enzyme sample from the previous column was applied to the top of the preformed gradient and centrifuged for 36 hours at 39,000 rpm in a SW40Ti rotor (Beckman). 0.25 ml fractions were collected from the bottom of the gradient tube and analyzed for enzymatic activity as well as purity by gel electrophoresis.

EXAMPLE 1

Enzyme Purification

Figure 1:
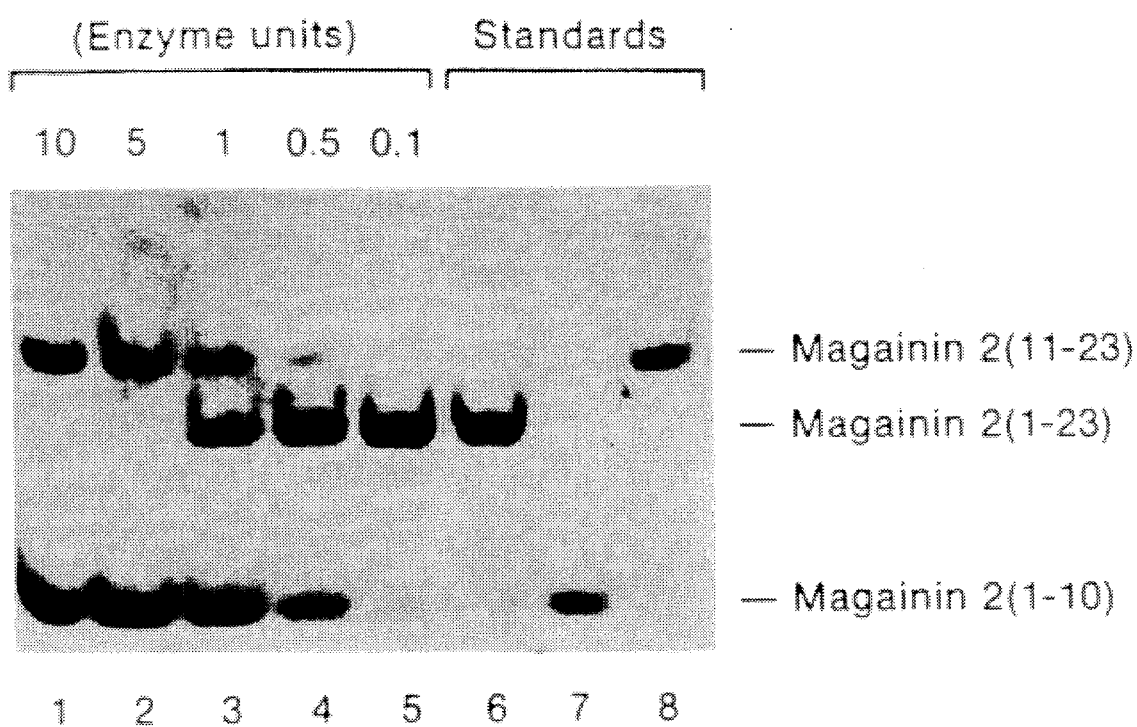
FIG. 1. Enzymatic Activity as Monitored by Acid Polyacrylamide Gel Electrophoresis Lanes 6–8 demonstrate the migration of synthetic full-length magainin 2 peptide and half-peptides on this 15% acrylamide acid gel prepared and run at pH 4 and stained with Coomassie Blue R-250 as described in Experimental Procedures. Results of cleavage reactions utilizing decreasing amounts of enzyme units are shown in lanes 1–5. One unit of enzyme activity (lane 3) is defined as described in Experimental Procedures.

Beginning with *Xenopus laevis* skin, the endopeptidase of this invention was purified to homogeneity by several chromatographic steps as described. Enzymatic activity was monitored by acidic polyarylamide gel electrophoresis (Gabriel, O., "Analytical disc gel electrophoresis," *Meth. Enzymol.* 22, 565–578 (1971); Boman, et al. "Chemical synthesis and enzymic processing of precursor forms of cecropins A and B.," *J Biol Chem.* 264, 5852–5860 (1989)) as depicted in FIG. 1. Differences in net electrostatic charge result in the resolution of full-length magainin 2-amide peptide substrate from the two cleavage products generated by hydrolysis. The gel displays increased production of half peptides with a concomitant decrease in the full-length substrate as additional units of enzymatic activity are added to a reaction (lanes 1–5). Both cleavage products comigrate precisely with the synthetic half-peptides run as standards on the gel (lanes 6–8).

Figure 2:
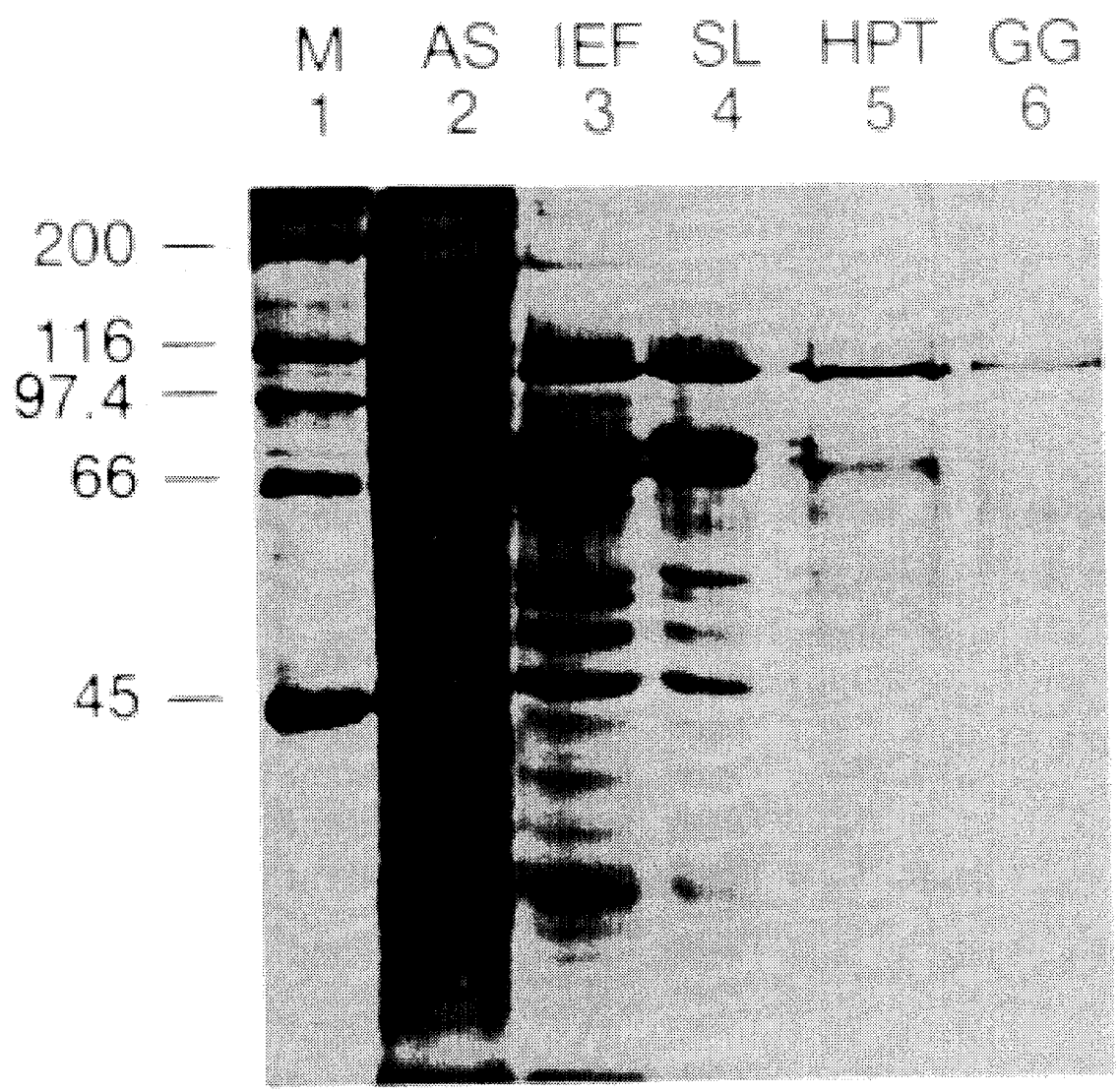
FIG. 2. SDS-Polyacrylamide Gel Electrophoresis of Enzyme Material at Each Stage of Purification Approximately 20 units of enzyme activity were loaded in each of lanes 2–5. This corresponds to 15 μg of the the ammonium sulfate fraction (lane 2), 1.5 μg of the isoelectric focusing fraction (lane 3), 1.0 μg of the Sephacryl S-300 fraction (lane 4), 0.5 μg of the hydroxylapatite fraction (lane 5), and 0.2 μg (10 U) of the glycerol gradient fraction (lane 6). The molecular weights ($\times 10^{-3}$) for marker proteins (Biorad) in lane 1 are indicated. Samples were electrophoresed as described in Experimental Procedures and stained with silver nitrate. The two faint bands migrating at approximately 60–65 kDa in lane 6 are artifacts commonly detected by silver stain methodology (Ochs, 1983).

A summary of the purification reveals that the endopeptidase was purified approximately one hundred-fold beginning with the ammonium sulfate fractionation step (Table 1). This relatively low fold-purification reflects the extreme abundance of the enzyme in Xenopus skin. FIG. 2 is a silver stained, sodium dodecyl sulfate acrylamide gel illustrating each purification step leading to the final homogenous species.

TABLE 1

PURIFICATION TABLE

| Purification Step | Volume (ml) | Protein (mg/ml) | Total Protein (mg) | Units/ml[a] | Total Units | Specific Activity | Yield (%) | Fold |
|---|---|---|---|---|---|---|---|---|
| Ammonium Sulfate | 3.6 | 15.00 | 54.00 | 20,000 | 72,000 | 1,333 | 100.0 | — |
| Isoelectric Focusing | 15.5 | 0.15 | 2.30 | 2250 | 34,875 | 15,163 | 48.0 | 11.4 |
| Sephacryl S-300 | 10.6 | 0.07 | 0.74 | 3000 | 31,800 | 43,000 | 44.0 | 32.3 |
| Hydroxylapatite | 4.2 | 0.03 | 0.126 | 4000 | 16,800 | 134,400 | 23.0 | 100.8 |
| Glycerol Gradient | 1.6 | 0.015 | 0.024 | 2000 | 3200 | 133,333[b] | 4.4 | 100.0 |

[a]One unit of enzyme activity as described in Experimental Procedures.
[b]The decrease in specific activity from the hydroxylapatite step to the glycerol gradient step is a result of quantitating only homogenous enzyme sample. Pure enzyme represents only a portion of the active material recovered following glycerol gradient fractionation.

EXAMPLE 2

Characterization of the endopeptidase

The endopeptidase was found to have a molecular weight of approximately 110,000. When electrophoresed under both reducing and non-reducing conditions, the protein band corresponded to enzymatic activity throughout every stage of purification and migrated to the same position, permitting the conclusion that the activity is comprised of a single subunit. Sedimentation of enzymatic activity in a glycerol gradient subjected to rate zonal centrifugation was consistent with a molecular mass of about 110 kD, providing further evidence that a monomeric species is responsible for endoproteolysis.

Inhibition studies employing several proteinase inhibitors suggest the endopeptidase is a member of the metalloprotease family of enzymes. While serine protease inhibitors such as leupeptin, phenylmethanesulfonyl fluoride (PMSF) and tosyl-L-phenylalanine chloromethyl ketone (TPCK), thiol protease inhibitor E-64 (N-[N-(L-3-trans-carboxyoxiran- 2-carbonyl)-L-leucyl]-agmatine), and the aspartyl protease inhibitor pepstatin exerted no effect on enzyme activity, ethylenediaminetetraacetic acid (EDTA) and 1,10-phenanthroline, the hallmark inhibitors of metalloproteases, substantially inhibited enzyme activity. Several other inhibitors such as bacitracin and phosphoramidon were also examined and found to have no effect on endoproteolysis. These results are summarized in Table 2.

The final enzyme purification step suggests that a single enzyme is responsible for cleaving several related peptide substrates. SDS-polyacrylamide gel electrophoresis of fractions recovered from a 15–30% glycerol gradient is displayed in FIG. 3A. Peak enzymatic activity against magainin 2-amide in fractions 27–30 revealed by acidic polyacrylamide gel electrophoresis (FIG. 3B) corresponds to the highly enriched protein band migrating at approximately 110 kilodaltons. Maximal endoproteolytic activity against two other natural antimicrobial peptides PGLa and XPF (xenopsin precursor fragment), correlates with the 110 kDa protein (FIG. 3C and 3D).

Characterization of each peptide's precise cleavage site allowed classification of the enzyme as an endopeptidase, i.e. a proteolytic enzyme capable of hydrolyzing peptide linkages initially in the interior of the peptide chain as well as terminal linkages. Reversed-phase HPLC followed by amino acid analyses of the major peptide peaks generated by incubation of pure enzyme with each substrate confirmed that the in vitro cleavage sites matched the cleavage sites of those identified in vivo. Giovannini et al., supra, (1987). As demonstrated in FIG. 4A and Table 3, the Lys-Lys peptide bond at residues ten and eleven of magainin 2-amide is hydrolyzed by the enzyme. HPLC chromatograms of cleavage reactions utilizing PGLa and XPF as substrates also indicate that a single proteolytic event is directed against each peptide (FIG. 4, B and C). Amino acid analyses of each reversed-phase peak confirmed that the endopeptidase cleaves the expected $Gly^{11}$-$Lys^{12}$ peptide bond of PGLa and XPF, as well as the analogous $Leu^{10}$-$Lys^{11}$ doublet present in CPF (data not shown). FIG. 11A summarizes the site of cleavage detected for each natural peptide substrate.

TABLE 2

INHIBITION PROFILE

| INHIBITOR | CONCENTRATION | % INHIBITION |
|---|---|---|
| Leupeptin | 1 mM | 0 |
| Pepstatin | 100 μm | 0 |
| PMSF | 10 mM | 0 |
| TPCK | 1 mM | 0 |
| E-64 | 300 μM | 0 |
| Bacitracin | 1 mg/ml | 0 |
| Phosphoramidon | 1 μM | 0 |
|  | 100 μM | 0 |
| EDTA | 0.5 mM | 25 |
|  | 5 mM | 25 |
|  | 50 mM | 50 |
| 1,10-Phenanthroline | 0.2 mM | 70 |
|  | 2 mM | 100 |
|  | 20 mM | 100 |

The % inhibitions listed above were determined by Coomassie Blue staining of acid gel electrophoresis following enzymatic assays utilizing magainin 2-amide as substrate. One unit of purified endopeptidase was incubated with inhibitor at the above concentrations for one hour and then incubated with native substrate under standard assay conditions.

TABLE 3

| Amino Acid | Observed Values | Expected Values* |
|---|---|---|
| (1) ANINO TERMINAL HALF-PEPTIDE | | |
| Gly | 1.16 | 1.12 (2) |
| Ile | 1.10 | 1.10 (1) |
| Lys | 0.78 | 0.89 (2) |
| Phe | 1.50 | 1.35 (1) |
| Leu | 1.02 | 1.03 (1) |

TABLE 3-continued

| Amino Acid | Observed Values | Expected Values* |
|---|---|---|
| His | 2.04 | 1.90 (1) |
| Ser | 1.42 | 1.27 (1) |
| Ala | 0.95 | 0.90 (1) |
| (2) CARBOXYL TERMINAL HALF-PEPTIDE | | |
| Gly | 1.10 | 1.12 (2) |
| Ile | 0.82 | 1.10 (1) |
| Lys | 0.91 | 0.89 (2) |
| Phe | 3.11 | 2.70 (2) |
| Ser | 1.17 | 1.27 (1) |
| Ala | 0.80 | 0.90 (1) |
| Val | 0.88 | 1.37 (1) |
| Glu | 0.93 | 0.70 (1) |
| Met | 1.71 | 1.45 (1) |
| Asn | 1.55 | 1.91 (1) |

Table 3. The Endopeptidase Cleaves Each Natural Substrate at a Single Xaa-Lys Bond
Amino acid analysis was conducted on each peak separated by reversed-phase HPLC (FIG. 4) as described in Experimental Procedures. Listed above are the results obtained from cleavage of magainin 2-amide.
*Expected value calculations were determined based on actual values obtained from hydrolysis of full-length magainin 2 peptide, and the prediction that cleavage products isolated by HPLC are identical to those observed in vivo (Giovaninni et al., 1987). Values in parentheses are expected number of residues.

EXAMPLE 3

The endopeptidase recognizes a particular substrate secondary structure

While magainin, PGLa, XPF and CPF all exhibit antimicrobial activity, these peptides do not share any extensive sequence homology. Only two residues are conserved across all four natural substrates so far demonstrated to undergo cleavage by the endopeptidase: a glycine at the amino terminus, and a lysine on the carboxyl side of the hydrolized bond.

Based on the data thus far presented, several possible determinants of substrate specificity could be envisioned. The endopeptidase may be employing a counting mechanism whereby it always cleaves the peptide bond located a particular number of residues from the terminus of a substrate, regardless of the nature of the peptide bond at that position. Another hypothesis is that endopeptidase activity is dictated solely by primary sequence. The majority of reports on endopeptidases attribute substrate specificity to the presence of a particular amino acid or sequence of residues. The putative dibasic recognition site, for example, is quite prevalent in neuropeptide and hormone precursor polypeptides that undergo multiple processing events, and much evidence supports the theory that endopeptidases recognize Lys-Arg or Arg-Arg doublets. Finally, another possibility involves the influence of substrate secondary structure on recognition and hydrolysis by an endoproteolytic enzyme.

To test the first hypothesis regarding a counting mechanism, magainin 2 analogues with truncations of either the amino or carboxyl terminus were utilized as substrates for the enzyme (see FIG. 11B for peptide sequences). If the endopeptidase was strictly measuring a certain number of amino acids from an end, each analogue should be hydrolyzed, yet the site of cleavage should be shifted. As illustrated in FIG. 5, slight cleavage of the Des-1 analogue was detected (lane 1), while amino-terminal truncation analogues of any greater length resisted attack (lanes 2–4). Deletion analogue, Des-1-3 is the most powerful demonstration that the endopeptidase does not invoke measuring of amino acids from an end. Deletion of the first three residues from the amino terminus of magainin 2 serves to translocate the $Gly^{13}$–$Lys^{14}$ doublet to positions 10–11, where the endopeptidase normally cleaves. Although Gly-Lys represents the natural cleavage sequence recognized in native PGLa, XPF and CPF, this magainin analogue was not hydrolyzed by the enzyme.

In contrast, the carboxyl-terminal deletions were all hydrolyzed to an extent comparable to the wildtype, even when as many as six residues were deleted (lanes 5–7). The common peptide fragment visualized in lanes 5, 6 and 7 comigrates with the native magainin 2 amino-terminal half-peptide (1–10). It was concluded that (1) the endopeptidase does not achieve its cleavage specificity by measuring from a peptide terminus, and (2) the determinant responsible for conferring recognition resides within the amino terminal portion of the magainin peptide.

In order to investigate which, if any, specific residues are critical for recognition and cleavage by the endopeptidase, a complete series of synthetic magainin 2 omission analogues was assayed. This experiment demonstrate in dramatic fashion that susceptibility to hydrolysis cannot be attributed to any one particular amino acid. Omission of any single amino acid from positions one through twelve of the magainin 2 sequence results in equally decreased levels of endoproteolysis (FIG. 6). On the other hand, analogues which constitute the omission of a single residue from position fourteen through twenty-three are hydrolyzed at wildtype levels. The omission of glycine 13 appears to confer an intermediate effect, which is perhaps explained by its position at the boundary of the substrate domain recognized by the endopeptidase for cleavage. FIG. 11C lists each peptide sequence and serves to highlight the fact that loss of activity may be attributed to the omission of residues as diverse as glycine, lysine and phenylalanine. The sole unifying characteristic is that each amino acid capable of rendering a substrate inactive through its omission resides in the amino terminal half of the peptide. In addition to ruling out the hypothesis that primary sequence is the sole determinant of substrate specificity, this data further supports the belief that magainin's recognition determinant is present within the first twelve residues of the peptide. Most compelling about these results however, is their suggestion that substrate secondary structure within this region influences susceptibility to hydrolysis by this novel endopeptidase.

EXAMPLE 4

Deduction of the structural motif recognized by the endopeptidase

Despite their negligible primary sequence homology, the natural magainin peptide substrates have been demonstrated to share structural features. Raman, NMR and circular dichroism spectroscopy have revealed that in a phospholipid bilayer the peptides adopt amphipathic, alpha-helical conformations. [Matsuzaki, et al. "Magainin 1-induced leakage of entrapped calcein out of negatively-charged lipid vesicles," Biochem. Biophys Acta 981, 130–134 (1989); Williams, et al. "Raman spectroscopy of synthetic antimicrobial frog peptides magainin 2a and PGLa," Biochem. 29, 4490–4496 (1990); Duclohier, et al. "Antimicrobial peptide magainin 1 from Xenopus skin forms anion-permeable channels in planar lipid bilayers," Biophys. J. 56, 1017–1021 (1989); and Bechinger, et al., "Orientations of amphipathic helical peptides in membrane bilayers determined by solid-state NMR spectroscopy," J. Biomol. NMR, in press] The potential alpha-helical nature of the amino-terminal domain of each substrate tested against the endopeptidase can be appreciated by examining helical wheels of these sequences. (FIG. 7). The continuous registry of hydrophobic residues constituting the nonpolar face of the amphipathic helix represents a recurrent motif, and the position of the endopeptidase cleavage site on the hydrophilic side signifies another shared feature of the natural substrates. Finally, the lysine residue located on the carboxyl side of the hydrolyzed bond projects from each helix in a similar orientation.

The results of the magainin 2 omission analogues (FIG. 6) can be explained when interpreted within this structural context. The omission of a single residue would not detract from the overall amphipathic nature of an alpha-helical conformation; however, the deletion of any amino acid within the first twelve would perturb the registry of hydrophobic residues along the nonpolar face, as well as their orientation with respect to the cleavage site. Based on the data thus far presented, the significance of secondary structure in governing substrate specificity was acknowledged.

EXAMPLE 5

Determination of the precise structural motif required for endoproteolysis

A direct assessment of the role of amphipathicity in substrate specificity was conducted by testing a series of magainin 2 glutamic acid substitution analogues. Twelve synthetic derivatives, each representing the replacement of amino acids 1–12 by a glutamic acid, were assayed for endoproteolysis (FIG. 11D). Substitution of those hydrophobic residues believed to reside along the hydrophobic face were predicted to render an analogue inactive, while substitutions serving to maintain the hydrophilic face of a putative alpha helix were not expected to profoundly affect substrate susceptibility. The results presented in FIG. 8A and B suggest that hydrophobicity is a crucial determinant of substrate-enzyme interaction. More specifically, the peptide became a less favorable substrate upon the replacement of a glutamate for the two hydrophobic residues surrounding the substrate cleavage site (Ala9 and Phe12, lanes 9 and 12) as well as for the amino-terminal glycine (lane 1); compare with lanes 6, 7 and 10 representing analogues cleaved at wild type levels. Decreased cleavage efficiency is also exhibited by analogues with glutamate substitutions at $Ile^2$ and $Phe^5$ (lanes 2 and 5). These particular residues when visualized as helical wheels (FIG. 8B) all reside on the nonpolar face of the helix. Conversely, with the exceptions of $Lys^4$ and $Lys^{11}$ (see below), substitutions of amino acids on the polar face of the helix do not significantly inhibit hydrolysis of a substrate.

If the endopeptidase were examining solely primary sequence surrounding the cleavage site, the effect of substitutions far upstream the hydrolyzed bond at amino acids 1, 2 and 5 should not be manifested. Furthermore, if the enzyme required only a certain peptide length relative to the cleavage site, unlike the magainin 2 omission analogues, glutamate substitutions should not hamper substrate cleavage. The apparent requirement of a particular substrate conformation emerges. The quantitative differences in substrate susceptibility exhibited in this Example serve to highlight those residues comprising the recognition motif. While the two hydrophobic residues bracketing the cleavage site appear to be most crucial, the three other nonpolar amino acids ($Gly^1$, $Ile^2$ and $Phe^5$) must also be involved, as their replacement with a charged residue affects hydrolysis. What unifies these seemingly random amino acids is their potential to generate a strongly hydrophobic surface within the amino-terminal domain of the magainin peptide when configured as an alpha-helix.

Three synthetic PGLa derivatives representing deletions of either $Lys^5$, $Gly^{11}$ or $Lys^{12}$ (see FIG. 11E for sequences) were tested against the endopeptidase to challenge the model of substrate secondary structure recognition. As demonstrated in FIG. 9A, the Des-$Lys^5$ analogue is cleaved as efficiently as native PGLa (lane 2), while the Des-$Gly^{11}$ PGLa derivative exhibits a definite decrease in endoproteolysis compared to native peptide (lane 4). The Des-$Lys^{12}$ analogue is completely resistant to hydrolysis as indicated by the equal intensity of uncleaved peptide in both the absence and presence of enzyme (compare lanes 5 and 6).

Examination of the helical wheel projections (FIG. 9B) of each derivative provides insight as to why the Des-Lys $^5$ derivative remains an ideal substrate but the Des-$Gly^{11}$ derivative exhibits compromised activity. Despite the deletion, the continuity of adjacent hydrophobic residues (designated by circles) in the Des-$Lys^5$ analogue remains intact, as does their position directly across the helix from the cleavage site (compare to native PGLa). This is not the case for the Des-$Gly^{11}$ analogue whereby the single omission results in the repositioning of $Lys^5$ (denoted by a square) within the array of hydrophobic amino acids. Analogous to the effect of replacing $Phe^5$ of magainin 2 with a glutamate (see FIG. 6), the endopeptidase exhibits decreased activity against this PGLa derivative. The Des-$Lys^{12}$ PGLa omission analogue constitutes the loss of the charged lysine on the carboxyl side of the scissile bond. Based on additional results reported below, it was concluded that this analogue is resistant to endoproteolysis because a charged residue at this position was required for cleavage.

EXAMPLE 6

Primary sequence at the cleavage site also determines sequence specificity

The presence of a conserved lysine residue on the carboxyl side of the cleaved bond of each natural peptide substrate suggests that primary sequence at the site of hydrolysis is a critical determinant of substrate specificity. In order to determine if any basic residue can fulfill this criterion, the magainin 1 analogue K11R constituting the replacement of all lysines with arginines was assayed (see FIG. 11G for peptide sequences). The peptide effectively served as a substrate confirming the prediction that any basic amino acid is tolerated by the enzyme for hydrolysis. The possibility that the endopeptidase is even less specific and requires simply a charged residue, either basic or acidic, at this position was already addressed by the magainin $Lys^{11}$ glutamic acid substitution (see FIG. 8). This derivative's resistance to cleavage allowed the conclusion that a basic amino acid is necessary for hydrolysis by the endopeptidase.

Definitive proof that a lysine or arginine is required for endoproteolysis was established by assaying several peptide analogues lacking any charged residues at the site of hydrolysis. The PGLa omission analogue Des-$Lys^{12}$ which results in a Gly-Ile doublet at the scissile bond exhibited no susceptibility to hydrolysis (see FIG. 9B, lane 6) first indicating the requirement of the lysine at this position. The magainin analogue K11A which represents a substitution of an alanine for the lysine at position 11 was assayed for cleavage and resisted attack, as was magainin analogue K11P which contains a proline in place of Lys11 (FIG. 11F).

Based on this data it was concluded that another determinant of substrate specificity is the presence of a basic residue on the carboxyl side of the scissile bond.

EXAMPLE 7

Any residue supportive of an alpha-helical conformation may occupy the amino-terminal side of the scissile bond Further characterization of the nature of the cleavage site entailed determining the limitations placed on the residue which comprises the amino-terminal side of the hydrolyzed bond. A survey of the residues present at this position in the substrates naturally synthesized by *Xenopus laevis* demonstrated the acceptance of lysine, glycine and leucine. Magainin 1 derivative G10A revealed that an alanine at this site was also compatible with cleavage, in accordance with the cleavage of PGLa analogue Des-Gly$^{11}$. Likewise, the magainin analogue containing a substitution of glutamic acid for glycine (G10E) at this position exhibited susceptibility to hydrolysis (see FIG. 8). The only tested amino acid found to be incompatible with cleavage by the endopeptidase was proline. The deleterious effect of introducing a proline into the substrate may be attributed to the fact that prolines serves to disrupt alpha helices.

The magainin 2 analogues dK11 and dK10, which represent substitutions of D-amino acids for Lys$^{11}$ and Lys$^{10}$ respectively, were assayed against the enzyme as well. Surprisingly, the endopeptidase cleaved these analogues (data summarized in FIG. 11H). The dK11 analogue was cleaved as efficiently as native substrate suggesting that despite the enzyme's requirement of a basic residue at that position, the chirality of the side chain was not critical for peptide susceptibility. The dK10 analogue on the other hand, which incorporates a D-Lysine on the amino terminal side of the scissile bond, exhibited a decrease in cleavage of approximately 50%.

The novel endopeptidase's demonstrated indifference to stereochemical specificity at the hydrolyzed peptide bond is an unusual feature of the enzymatic reaction. Several similar investigations into the stereochemical requirements of amino acids at an endoproteolytic cleavage site report the complete inactivity of substrates which contain D-amino acids (Checler et al., 1986; Clamagirand et al., 1987).

EXAMPLE 8

Substrate structural motif is recognized by the endopeptidase as an autonomous domain The magainin 2 synthetic analogue REVR (1–4) possessing a four residue amino-terminal extension (see FIG. 11H) was also tested against the purified endopeptidase. This analogue was cleaved with approximately 50% efficiency relative to native magainin 2, and HPLC and amino acid analyses confirmed that hydrolysis occurs at the same unique Lys$^{10}$–Lys$^{11}$ bond (now present in positions 14 and 15). Because the cleavage site was faithfully recognized despite the presence of four extra residues at the amino terminus, the earlier conclusion that the endopeptidase does not employ a measuring mechanism was further confirmed. In addition, hydrolysis of this analogue indicates that the secondary structural domain recognized by the enzyme may be regarded as an autonomous motif; as long as the substrate is capable of adopting the requisite conformation upon interaction with the enzyme, additional structure introduced nearby does not appear to severely compromise endoproteolysis.

EXAMPLE 9

Inactive substrates with proper structural motif still demonstrate ability to bind endopeptidase Through the course of extensive substrate specificity analyses, several synthetic analogues did not serve as substrates for endoproteolysis. The Des-1–4 amino-terminal truncation analogue of magainin 2 was utilized in inhibition assays designed to distinguish between these two possibilities. As illustrated in FIG. 10, preincubation of the analogue with the endopeptidase at a tenfold molar excess efficiently served to inhibit cleavage of magainin 2 (compare lanes 2 and 3). Furthermore, the Des-1–4 analogue was found to inhibit endoproteolysis against PGLa, XPF and CPF (data not shown) offering additional support that a single endopeptidase activity cleaves multiple peptide substrates. This phenomenon suggests that despite the loss of four residues from the amino terminus resulting in the alteration of the structural motif required by the endopeptidase for cleavage, the initial binding reaction involves less stringent structural parameters.

Although unrelated to the magainins, melittin, an alpha-helical cytolytic peptide isolated from bee venom, exhibits ionophoric properties much like the magainins (Tosteson and Tosteson, 1981). These functional similarities may result from their shared structural features, and the ability of the endopeptidase to treat melittin as a substrate was assessed. Examination of its primary sequence (Table II) allowed the prediction that melittin would not be cleaved as it does not contain the requisite basic residue at the proper location on the hydrophilic face of the helix (FIG. 10, lane 4). Melittin was also tested as an inhibitor of enzymatic activity against the natural substrate magainin 2. Preincubation of the endopeptidase with a tenfold molar excess of melittin (FIG. 10, lane 6) served to inhibit cleavage, but only to a degree of approximately 25%. This was attributed to limited inhibitory capability to a lowered binding affinity (compared to magainin Des-1–4) for the endopeptidase, perhaps due to the presence of a proline at residue fourteen. These results lead to the postulation that the maintenance of an uninterrupted alpha helix is necessary not only for cleavage by the endopeptidase, but for efficient binding as well.

We claim:

1. A composition comprising, a substantially pure endopeptidase endogenous to biological cells of the skin of *Xenopus laevis* having a molecular weight of about 110,000 daltons as measured by SDS PAGE and enzymatic activity and substrate specificity characterized by:

(a) enzyme activity which is substantially uninhibited by phenylmethanesulfonyl fluoride (PMSF) at a concentration of 10 mM, tosyl-L-phenylalanine chloromethyl ketone (TPCK) at a concentration of 1 mM, E-64 at a concentration of 300 μM, leupeptin at a concentration of 1 mM, bacitracin at a concentration of 1 mg/ml, phosphoramidon at a concentration of 1 μM and pepstatin at a concentration of 100 μM;

(b) enzyme activity which is inhibited by at least about 25 percent by EDTA at a concentration of at least about 0.5 mM and inhibited at least about 70 percent by 1,10-phenanthroline at a concentration of at least 0.2 mM; and (c) an enzymatic activity which cleaves peptide substrates comprising an alpha helical structure of at least about twelve to fourteen amino acids wherein said helical structure has a hydrophobic face and a hydrophilic face, said cleavage occurring amino terminal to a basic amino acid residue on the hydrophilic face positioned within the context of at least four nonpolar amino acids substantially aligned along the hydrophobic face of the helical structure.

2. The composition according to claim 1 wherein said substantially pure endopeptidase is isolated from *Xenopus laevis* skin.

3. The composition according to claim 1 wherein the peptide substrate the endopeptidase cleaves is magainin, PGLa, xenopsin precursor fragment (XPF) or caerulein precursor fragment (CPF).

4. The endopeptidase produced by the method comprising the steps of:

(a) culturing recombinant host cells transformed with a DNA sequence coding for the endopeptidase of claim 1 operably linked to appropriate regulatory control sequences which sequences are capable of effecting the expression of said coding sequence in said transformed cells; and (b) recovering said expressed endopeptidase.

5. The composition of claim 1 wherein the basic amino acid is lysine.

6. The composition of claim 1 wherein the basic amino acid is arginine.

* * * * *